United States Patent
Cherubini et al.

(10) Patent No.: US 12,190,512 B2
(45) Date of Patent: Jan. 7, 2025

(54) COMPUTER-IMPLEMENTED SYSTEMS AND METHODS FOR ANALYZING EXAMINATION QUALITY FOR AN ENDOSCOPIC PROCEDURE

(71) Applicant: Cosmo Artificial Intelligence—AI Limited, Dublin (IE)

(72) Inventors: Andrea Cherubini, Rome (IT); Pietro Salvagnini, Padua (IT); Nhan Ngo Dinh, Rome (IT)

(73) Assignee: COSMO ARTIFICIAL INTELLIGENCE—AI LIMITED, Dublin (IE)

( * ) Notice: Subject to any disclaimer, the term of this patent is extended or adjusted under 35 U.S.C. 154(b) by 0 days.

(21) Appl. No.: 17/961,764

(22) Filed: Oct. 7, 2022

(65) Prior Publication Data

US 2023/0110263 A1  Apr. 13, 2023

Related U.S. Application Data

(60) Provisional application No. 63/253,700, filed on Oct. 8, 2021.

(51) Int. Cl.
| | | |
|---|---|---|
| G06T 15/00 | (2011.01) | |
| A61B 1/00 | (2006.01) | |
| G06T 7/00 | (2017.01) | |

(52) U.S. Cl.
CPC ...... *G06T 7/0012* (2013.01); *A61B 1/000094* (2022.02); *G06T 2207/10068* (2013.01)

(58) Field of Classification Search
CPC ......... G06T 7/0012; G06T 11/00; G06T 7/73; G06T 7/11; G06T 7/155;

(Continued)

(56) References Cited

U.S. PATENT DOCUMENTS 9,959,615 B2 * 5/2018 Liang .................. G16H 50/20
11,026,837 B2 * 6/2021 Hipsley ............... A61F 9/00825
(Continued)

FOREIGN PATENT DOCUMENTS

WO  2020242949 A1  12/2020
WO  2021156159 A1  8/2021

OTHER PUBLICATIONS

Fu Z, Jin Z, Zhang C, He Z, Zha Z, Hu C, Gan T, Yan Q, Wang P, Ye X. The future of endoscopic navigation: A review of advanced endoscopic vision technology. IEEE Access. Mar. 10, 2021;9:41144-67.*

(Continued)

*Primary Examiner* — Phu K Nguyen

(57) ABSTRACT

A computer-implemented system is provided that includes at least one processor that is adapted to analyze a plurality of frames from a real-time video to identify frames during which an operator is interacting with an image device to examine areas of a patient. The at least one processor is further configured to generate, from the identified frames, data representations of a first area examined by the operator interacting with the image device and further generate data representations of one or more further areas examined by the operator interacting with the image device. The at least one processor is also configured to aggregate the data representations of the first area with the data representations of the one or more further areas and determine, using the aggregated data representations, an examination quality level of the areas examined by the operator and present, on a display device during the medical procedure, a graphical representation indicating the examination quality level of the areas examined by the operator.

26 Claims, 15 Drawing Sheets

(58) Field of Classification Search
CPC ........... G06T 2207/30032; G06T 2207/20076;
G06T 2207/10016; G06T 2207/20084;
G06T 2207/30096; G06T 2210/41; G06T
2207/30028; G06T 2207/10068; G16H
15/00; G16H 30/40; G06V 20/47; G06V
20/44
USPC ......................................................... 345/418
See application file for complete search history.

(56) References Cited

U.S. PATENT DOCUMENTS

| | | | |
|---|---|---|---|
| 11,687,800 B2* | 6/2023 | Bonutti | A61B 5/163 706/11 |
| 2011/0301447 A1 | 12/2011 | Park et al. | |
| 2018/0225820 A1 | 8/2018 | Liang et al. | |
| 2021/0280312 A1 | 9/2021 | Freedman et al. | |
| 2021/0338484 A1* | 11/2021 | Hipsley | A61F 9/00825 |
| 2023/0007982 A1* | 1/2023 | Cherubini | G06T 7/73 |
| 2023/0110263 A1* | 4/2023 | Cherubini | A61B 1/000096 345/418 |
| 2024/0020835 A1* | 1/2024 | Cherubini | G06T 7/0012 |

OTHER PUBLICATIONS

Brandao, Patrick. "Enhancing endoscopic navigation and polyp detection using artificial intelligence." PhD diss., UCL (University College London), 2021.*

Armin et al., Automated visibility map of the internal colon surface from colonoscopy video, International Journal of Computer Assisted Radiology and Surgery, vol. 11, No. 9, pp. 1599-1610, Springer, ISSN: 1861-6410, DOI: 10.1007/s11548-016-1462-8, Published online: Aug. 4, 2016, 12 pages.

International Search Report and Written Opinion, PCT/IB2022/059632, dated Mar. 27, 2023, 23 pages.

* cited by examiner

COMPUTER-IMPLEMENTED SYSTEMS AND METHODS FOR ANALYZING EXAMINATION QUALITY FOR AN ENDOSCOPIC PROCEDURE

CROSS REFERENCE TO RELATED APPLICATION(S)

This application claims priority to U.S. Provisional Application No. 63/253,700, filed Oct. 8, 2021, the contents of which is hereby incorporated by reference in its entirety.

TECHNICAL FIELD

The present disclosure relates generally to the field of imaging systems and computer-implemented systems and methods for processing video from an imaging system or device. More specifically, and without limitation, this disclosure relates to systems, methods, and computer-readable media for processing frames of video from an imaging device and performing an analysis, such as an examination quality analysis. The systems and methods disclosed herein may be used in various applications, including during a medical procedure for examining a patient. The systems and methods disclosed herein may also be implemented to provide real-time image processing capabilities, such as determining and providing an examination quality level analysis in real-time during a procedure utilizing a medical imaging device.

BACKGROUND

Modern medical procedures require precise and accurate examination of a patient's body and organs. For example, the rate of detection of malignancies during an endoscopy may increase when an operator of an endoscope examines each area in the colon carefully and thoroughly. Conversely, a malignancy may be missed if the operator inadvertently skips or otherwise examines an area of the patient's body poorly. Several factors may affect the operator's level of examination, including skill, fatigue level, and memory recall as to whether a particular area has been examined.

Various medical imaging and examination systems have heretofore been developed, but many suffer from one or more disadvantages or drawbacks. For example, extant solutions fail to provide any analysis or visual feedback for the operator as to the quality or level of examination of a particular area. Additionally, extant systems and methods fail to provide real-time analysis and feedback of an operator's examination technique, which may aid the operator in correcting his or her technique while examining a patient's body or organs. Furthermore, extant systems and methods fail to evaluate or provide feedback not only as to the examination of particular area(s), but also as to the entire medical procedure or a portion thereof.

Therefore, there is a need for improvements in imaging systems and methods, including those used in medical procedures where a patient is examined. Among other things, there is a need for providing computer-implemented analysis and feedback on the quality or level of an operator's examination technique during, for example, a medical procedure. Computer-implemented systems and methods are also needed for analyzing data and determining examination quality levels in real-time when navigating and examining a patient's body or organs. Embodiments of the present disclosure provide such improvements and can address one or more of the above-noted drawbacks or disadvantages of extant solutions.

SUMMARY

Embodiments of the present disclosure include systems, methods, and computer-readable media for analyzing examination quality during a medical procedure, such as endoscopy. Consistent with some disclosed embodiments, systems, methods, and computer-readable media are provided for processing frames of a video and performing surface exposure, trajectory, and/or speed analysis during, for instance, an endoscopic procedure. Embodiments of the present disclosure also relate to systems and methods for identifying interactions of an operator with an image device and determining examination quality levels in real-time when the operator examines a patient's body or organs. As disclosed herein, an examination quality level analysis may be based on a combination of factors, such as exposure, trajectory, and/or speed. One or more of these factors, including exposure, trajectory, and/or speed, may be individually or jointly presented to the operator while the patient's body or organs are examined. These and other embodiments, features, and implementations are described herein.

Consistent with the present disclosure, a system of one or more computers can be configured to perform operations or actions by virtue of having software, firmware, hardware, or a combination of them installed for the system that in operation causes or cause the system to perform those operations or actions. One or more computer programs can be configured to perform operations or actions by virtue of including instructions that, when executed by data processing apparatus (such as one or more processors), cause the apparatus to perform such operations or actions.

One general aspect includes a computer-implemented system for processing a video captured during a medical procedure, such as endoscopy. The computer-implemented system may include at least one processor configured to receive a video captured from an image device during a medical procedure performed on a patient, the video including a plurality of frames. The at least one processor may be further configured to: analyze the plurality of frames to identify frames during which an operator is interacting with the image device to examine areas of the patient for analysis; generate, from the identified frames, data representations of a first area examined by the operator interacting with the image device; further generate, from the identified frames, data representations of one or more further areas examined by the operator interacting with the image device; and aggregate the data representations of the first area with the data representations of the one or more further areas. Further, the at least one processor may be configured to determine, using the aggregated data representations, an examination quality level of the areas examined by the operator; and present, on a display device, a graphical representation indicating the determined examination quality level of the areas examined by the operator. Other embodiments include corresponding computer methods, apparatus, and computer programs recorded on one or more computer storage devices, each configured to perform the above operations or features.

Implementations may include one or more of the following features. The examination quality level may be based on one or more of a trajectory of the image device, a speed of the image device, and/or a ratio between the areas examined by the operator and an area of a model surface. The data representations for the first area and the one or more further areas may include at least one of two-dimensional data and three-dimensional data. The system may include a neural network adapted to perform a contextual evaluation to identify frames among the plurality of frames during which the operator is interacting with the image device to examine areas of the patient for analysis.

The at least one processor may be further configured to determine the examination quality level on a real-time basis during the medical procedure and update the determined examination quality level as the medical procedure is performed on the patient. The at least one processor may be further configured to modify the graphical representation as the determined examination quality level is updated during the medical procedure. Further, the at least one processor may be configured to modify at least one of a color, a pattern, an image, a video, or an alphanumeric character of the graphical representation. The at least one processor may be further configured to determine a short-term examination quality level for an area examined by the operator, and a long-term examination quality level for a plurality of areas examined by the operator during the medical procedure performed on the patient. The medical procedure may include at least one of an endoscopy, an esophagogastroduodenoscopy, a colonoscopy, a sigmoidoscopy, an endoscopic cholangiopancreatography, or an enteroscopy. The examined areas during the medical procedure may include portions of the colon of the patient.

The at least one processor may be further configured to: generate, from the identified frames, a first three-dimensional representation of an examined first area of the patient; further generate, from the identified frames, a second three-dimensional representation of an examined second area of the patient; determine a proximity of the first three-dimensional representation to the second three-dimensional representation in three-dimensional space; merge at least a portion of the first three-dimensional representation with at least a portion of the second three-dimensional representation when the determined proximity is within a threshold; and identify, using the merged portions of the first and second three-dimensional representations, areas of the patient not examined by the operator during the medical procedure. Implementations of the described techniques may include hardware, a method or process, or computer software on a computer-accessible medium.

Another general aspect includes a computer-implemented system for processing video captured during a medical procedure. The computer-implemented system may comprise at least one processor configured to receive a video captured from an image device during a medical procedure performed on a patient, the video including a plurality of frames. The at least one processor may be further configured to analyze the plurality of frames to identify frames during which an operator is interacting with the image device to examine areas of the patient for analysis, and generate, from the identified frames, data representations of each local area examined by the operator interacting with the image device. Further, the at least one processor may be configured to: determine, using the data representations for each local area, a short-term examination quality level for the portions examined by the operator; and present, on a display device during the medical procedure, a graphical representation indicating the short-term examination quality level for each local area examined by the operator. Other embodiments include corresponding computer methods, apparatus, and computer programs recorded on one or more computer storage devices, each configured to perform the above operations or features.

Implementations may include one or more of the following features. The data representations for each local area may be aggregated by the at least one processor and the short-term examination quality level may be determined by the at least one processor using the aggregated data representations. Additionally, or alternatively, in the computer-implemented system, the short-term examination quality level may be based on at least one of a trajectory of the image device, a speed of the image device, or surface exposure. Surface exposure may be based on a ratio between the areas examined by the operator and an area of a model surface. The at least one processor may be further configured to aggregate data representations of a plurality of local areas examined by the operator into a long-term data representation. The at least one processor may be further configured to determine a long-term examination quality level based on the long-term data representation, the long-term examination quality level indicating the total amount of examined areas over the entire medical procedure. The data representations of the plurality of local areas may include two-dimensional data and three-dimensional data, and the at least one processor may be further configured to construct at least a model of each local area using a point cloud. The system may include a neural network adapted to perform a contextual evaluation to identify frames among the plurality of frames during which the operator is interacting with the image device to examine areas of the patient for analysis.

The at least one processor may be further configured to determine, for each identified frame, at least one of a depth, a camera position, or edges. The at least one processor may be further configured to determine the short-term examination quality level on a real-time basis during the medical procedure and update the determined short-term examination quality level as the medical procedure is performed on the patient. The at least one processor may be further configured to modify the graphical representation as the determined short-term examination quality level is updated during the medical procedure. The at least one processor may be further configured to modify at least one of a color, a pattern, an image, a video, or an alphanumeric character of the graphical representation. The medical procedure may include at least one of an endoscopy, an esophagogastroduodenoscopy, a colonoscopy, a sigmoidoscopy, an endoscopic cholangiopancreatography, or an enteroscopy. The examined areas during the medical procedure may include portions of the colon of the patient.

Systems and methods consistent with the present disclosure may be implemented using any suitable combination of software, firmware, and hardware. Implementations of the present disclosure may include programs or instructions that are machine constructed and/or programmed specifically for performing functions associated with the disclosed operations or actions. Still further, non-transitory computer-readable storage media may be used that store program instructions, which are executable by at least one processor to perform the steps and/or methods described herein.

It will be understood that the foregoing general description and the following detailed description are exemplary and explanatory only, and are not restrictive of the disclosed embodiments.

BRIEF DESCRIPTION OF THE DRAWINGS

The following drawings which comprise a part of this specification, illustrate several embodiments of the present disclosure and, together with the description, serve to explain the principles and features of the disclosed embodiments. In the drawings.

DETAILED DESCRIPTION

Figure 1:
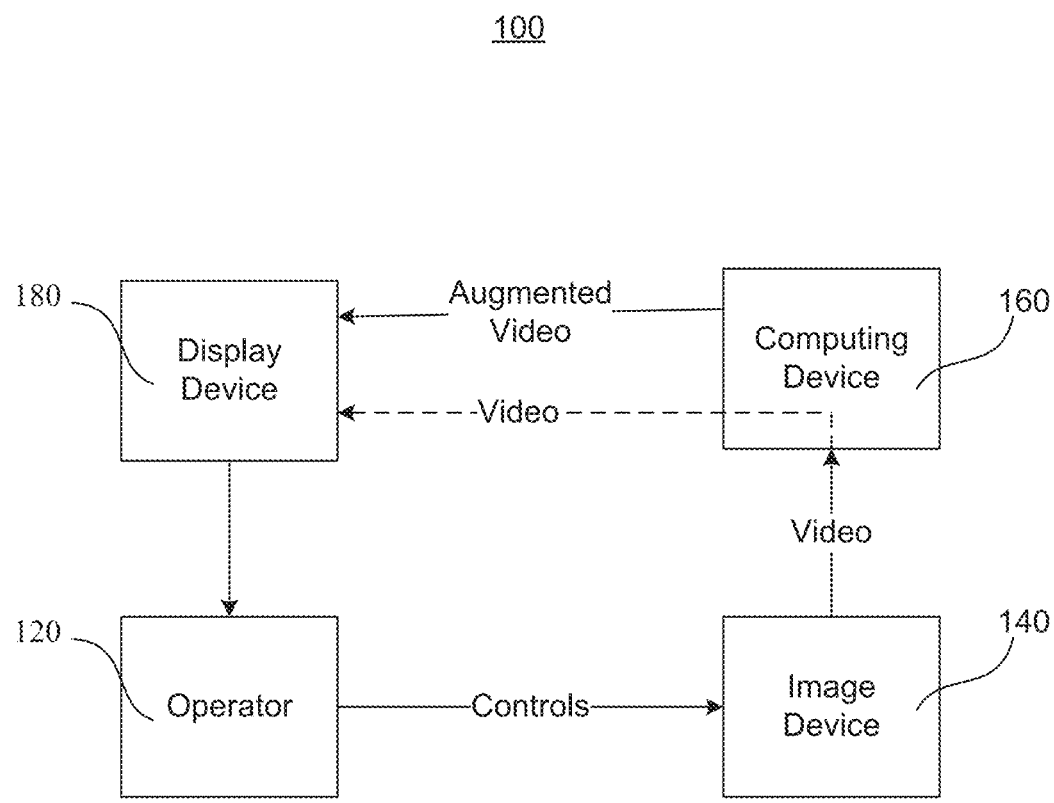
FIG. 1 is a schematic representation of an example computer-implemented system for processing real-time video, consistent with embodiments of the present disclosure.

Example embodiments are described below with reference to the accompanying drawings. The figures are not necessarily drawn to scale. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It should also be noted that as used herein and in the appended claims, the singular forms "a," "an," and "the" include plural references unless the context clearly dictates otherwise.

In the following description, various working examples are provided for illustrative purposes. However, it will be appreciated that the present disclosure may be practiced without one or more of these details.

Throughout this disclosure there are references to "disclosed embodiments," which refer to examples of inventive ideas, concepts, and/or manifestations described herein. Many related and unrelated embodiments are described throughout this disclosure. The fact that some "disclosed embodiments" are described as exhibiting a feature or characteristic does not mean that other disclosed embodiments necessarily share that feature or characteristic.

Embodiments described herein include non-transitory computer readable medium containing instructions that when executed by at least one processor, cause the at least one processor to perform a method or set of operations. Non-transitory computer readable mediums may be any medium capable of storing data in any memory in a way that may be read by any computing device with a processor to carry out methods or any other instructions stored in the memory. The non-transitory computer readable medium may be implemented as software, firmware, hardware, or any combination thereof. Software may preferably be implemented as an application program tangibly embodied on a program storage unit or computer readable medium consisting of parts, or of certain devices and/or a combination of devices. The application program may be uploaded to, and executed by, a machine comprising any suitable architecture. Preferably, the machine may be implemented on a computer platform having hardware such as one or more central processing units ("CPUs"), a memory, and input/output interfaces. The computer platform may also include an operating system and microinstruction code. The various processes and functions described in this disclosure may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium may be any computer readable medium except for a transitory propagating signal.

The memory may include any mechanism for storing electronic data or instructions, including Random Access Memory (RAM), a Read-Only Memory (ROM), a hard disk, an optical disk, a magnetic medium, a flash memory, other permanent, fixed, volatile or non-volatile memory. The memory may include one or more separate storage devices collocated or disbursed, capable of storing data structures, instructions, or any other data. The memory may further include a memory portion containing instructions for the processor to execute. The memory may also be used as a working memory device for the processors or as a temporary storage.

Some embodiments may involve at least one processor. A processor may be any physical device or group of devices having electric circuitry that performs a logic operation on input or inputs. For example, the at least one processor may include one or more integrated circuits (IC), including application-specific integrated circuit (ASIC), microchips, microcontrollers, microprocessors, all, or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory.

In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Embodiments consistent with the present disclosure may involve a network. A network may constitute any type of physical or wireless computer networking arrangement used to exchange data. For example, a network may be the Internet, a private data network, a virtual private network using a public network, a Wi-Fi network, a local area network ("LAN"), a wide area network ("WAN"), and/or other suitable connections that may enable information exchange among various components of the system. In some embodiments, a network may include one or more physical links used to exchange data, such as Ethernet, coaxial cables, twisted pair cables, fiber optics, or any other suitable physical medium for exchanging data. A network may also include one or more networks, such as a private network, a public switched telephone network ("PSTN"), the Internet, and/or a wireless cellular network. A network may be a secured network or unsecured network. In other embodiments, one or more components of the system may communicate directly through a dedicated communication network. Direct communications may use any suitable technologies, including, for example, BLUETOOTH™, BLUETOOTH LE™ (BLE), Wi-Fi, near field communications (NFC), or other suitable communication methods that provide a medium for exchanging data and/or information between separate entities.

In some embodiments, machine learning networks or algorithms may be trained using training examples, for example in the cases described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning network or algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. The training may be supervised or non-supervised, or a combination thereof. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by a process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters. The machine learning networks or algorithms may be further retrained based on any output.

Certain embodiments disclosed herein may include computer-implemented systems for performing operations or methods comprising a series of steps. The computer-implemented systems and methods may be implemented by one or more computing devices, which may include one or more processors as described herein, configured to process real-time video. The computing device may be one or more computers or any other devices capable of processing data. Such computing devices may include a display such as an LCD display, augmented reality (AR), or virtual reality (VR) display. However, the computing device may also be implemented in a computing system that includes a back end component (e.g., as a data server), or that includes a middleware component (e.g., an application server), or that includes a front end component (e.g., a user device having a graphical user interface or a Web browser through which a user can interact with an implementation of the systems and techniques described here), or any combination of such back end, middleware, or front end components. The components of the system and/or the computing device can be interconnected by any form or medium of digital data communication (e.g., a communication network). Examples of communication networks include a LAN network, a WAN network, and the Internet. The computing device can include clients and servers. A client and server are generally remote from each other and typically interact through a communication network. The relationship of client and server arises by virtue of computer programs running on the respective computers and having a client-server relationship to each other.

FIG. 1 illustrates an example computer-implemented system 100 for processing real-time video, according to embodiments of the present disclosure. As shown in FIG. 1, system 100 includes an image device 140 and an operator 120 who operates and controls image device 140 through control signals sent from operator 120 to image device 140. By way of example, in embodiments where the video feed comprises a medical video, operator 120 may be a physician or other health care professional that performs a medical procedure on a patient. Image device 140 may comprise a medical imaging device, such as an endoscopy imaging device, an X-ray machine, a computed tomography (CT) machine, a magnetic resonance imaging (MRI) machine, or any other medical imaging device that produces videos or one or more images of a human body or a portion thereof. Operator 120 may interact with and control image device 140 during a medical procedure performed on a patient by controlling, among other things, a capture rate of image device 140 and/or a movement or navigation of image device 140, e.g., through or relative to the human body of a patient or individual. In some embodiments, image device 140 may comprise a swallowable capsule device or other form of capsule endoscopy device as opposed to a conventional endoscopy imaging device inserted through a cavity of the human body.

In the example of FIG. 1, during a medical procedure performed on a patient, image device 140 may transmit the captured video as a plurality of image frames to a computing device 160. Computing device 160 may comprise one or more processors to process the video, as described herein (see, e.g., FIG. 2). In some embodiments, the one or more of the processors may be implemented as separate component(s) (not shown) that are not part of computing device 160 but in network communication therewith. In some embodiments, the one or more processors of computing device 160 may implement one or more networks, such as trained neural networks. Examples of neural networks include an object detection network, a classification detection network, an interaction detection network, and/or other networks. Computing device 160 may receive and process the plurality of image frames from image device 140. In some embodiments, control or information signals may be exchanged between computing device 160 and operator 120 for purposes for controlling, instructing and/or causing the creation of one or more augmented videos. These control or information signals may be communicated as data through image device 140 or directly from operator 120 to computing device 160. Examples of control and information signals include signals for controlling components of computing device 160, such as the machine learning algorithms described herein.

In the example of FIG. 1, computing device 160 may process and augment the video received from image device 140 and then transmit the augmented video to a display device 180. In some embodiments, the video augmentation or modification may comprise providing one or more overlays, alphanumeric characters, shapes, diagrams, images, animated images, or any other suitable graphical representation in or with the video frames. As depicted in FIG. 1, computing device 160 may also be configured to relay the original, non-augmented video from image device 140 directly to display device 180. For example, computing device 160 may perform a direct relay under predetermined conditions, such as when there is no overlay or other augmentation or modification to be generated. In some embodiments, computing device 160 may perform a direct relay if operator 120 transmits a command as part of a control signal to computing device 160 to do so. The commands from operator 120 may be generated by operation of button(s) and/or key(s) included on an operator device and/or an input device (not shown), such as a mouse click, a cursor hover, a mouseover, a button press, a keyboard input, a voice command, an interaction performed in virtual or augmented reality, or any other input.

To augment the video, computing device 160 may process the video from image device 140 alone or together with control or information signals from operator 120 and create a modified video stream to send to display device 180. The modified video may comprise the original image frames with the augmenting information to be displayed to the operator via display device 180. The augmenting information may include one or more graphical representations of a determined examination quality level or value, alone or in combination with other information, such as exposure, speed, and/or trajectory information. In the modified video stream, the graphical representation(s) may be overlaid on the video and placed away from the main camera view or field of view (e.g., in an upper or lower corner of the display or another position that does not obstruct the main camera view or field of view). In some embodiments, the graphical representation(s) may be selectively displayed (e.g., in response to ON/OFF or other control signals from the operator) and/or presented in a separate panel or display (i.e., a separate video output and not as an overlay to the real-time video from the image device 140). Display device 180 may comprise any suitable display or similar hardware for displaying the video or modified video, such as an LCD, LED, or OLED display, an augmented reality display, or a virtual reality display.

Figure 2:
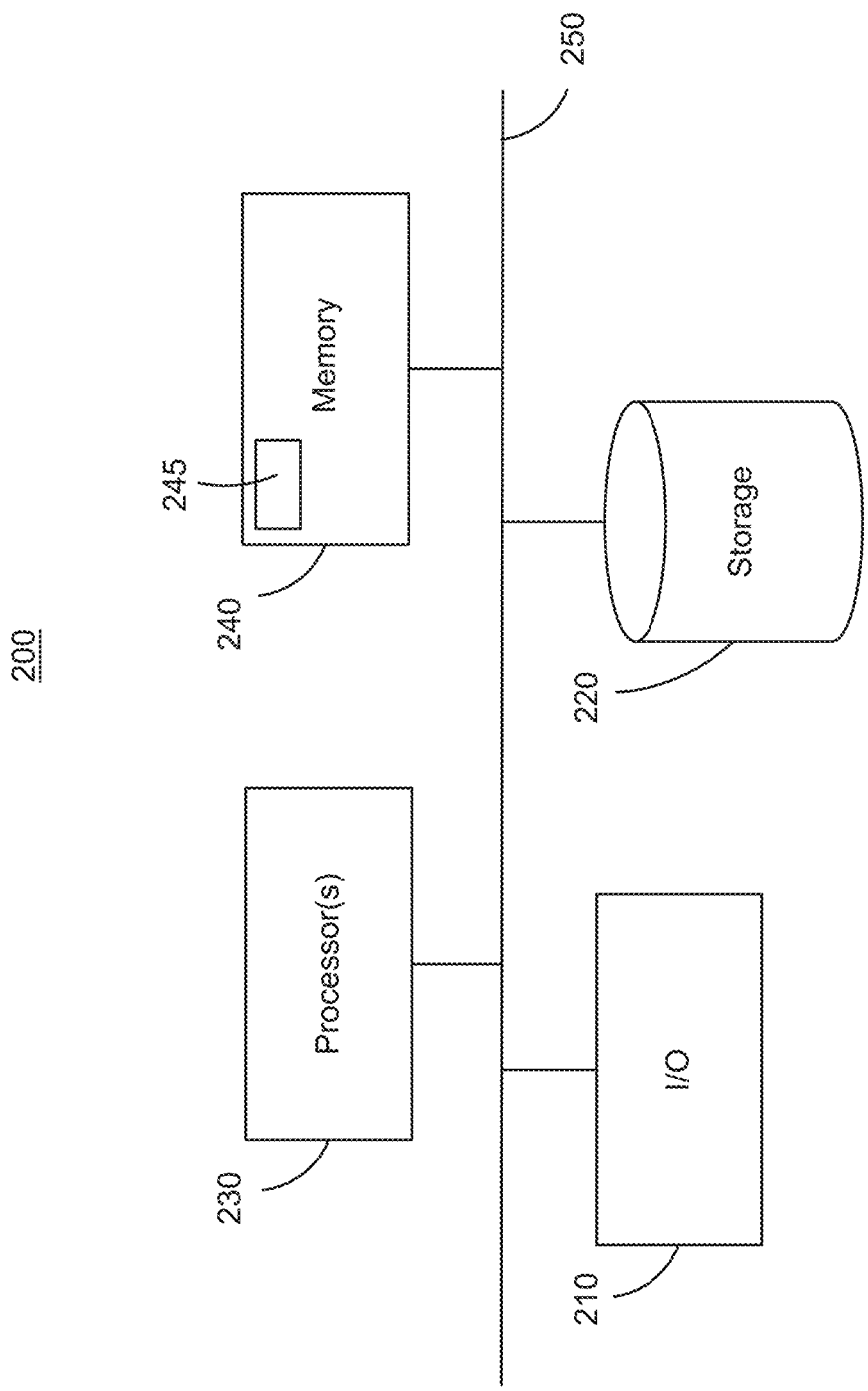
FIG. 2 illustrates an example computing device which may be employed in connection with the example system of FIG. 1 and other embodiments of the present disclosure.

FIG. 2 illustrates an example computing device 200 for processing real-time video, consistent with embodiments of the present disclosure. Computing device 200 may be used in connection with the implementation of the example system of FIG. 1 (including, e.g., computing device 160). It is to be understood that in some embodiments the computing device may include multiple sub-systems, such as cloud computing systems, servers, and/or any other suitable components for receiving and processing real-time video.

As shown in FIG. 2, computing device 200 may include one or more processor(s) 230, which may include, for example, one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations, as noted above. In some embodiments, processor(s) 230 may include, or may be a component of, a larger processing unit implemented with one or more processors. The one or more processors 230 may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

As further shown in FIG. 2, processor(s) 230 may be communicatively connected via a bus or network 250 to a memory 240. Bus or network 250 may be adapted to communicate data and other forms of information. Memory 240 may include a memory portion 245 that contains instructions that when executed by the processor(s) 230, perform the operations and methods described in more detail herein. Memory 240 may also be used as a working memory for processor(s) 230, a temporary storage, and other memory or storage roles, as the case may be. By way example, memory 240 may be a volatile memory such as, but not limited to, random access memory (RAM), or non-volatile memory (NVM), such as, but not limited to, flash memory.

Processor(s) 230 may also be communicatively connected via bus or network 250 to one or more I/O device 210. I/O device 210 may include any type of input and/or output device or periphery device. I/O device 210 may include one or more network interface cards, APIs, data ports, and/or other components for supporting connectivity with processor(s) 230 via network 250.

As further shown in FIG. 2, processor(s) 230 and the other components (210, 240) of computing device 200 may be communicatively connected to a database or storage device 220. Storage device 220 may electronically store data in an organized format, structure, or set of files. Storage device 220 may include a database management system to facilitate data storage and retrieval. While illustrated in FIG. 2 as a single device, it is to be understood that storage device 220 may include multiple devices either collocated or distributed. In some embodiments, storage device 220 may be implemented on a remote network, such as a cloud storage.

Processor(s) 230 and/or memory 240 may also include machine-readable media for storing software or sets of instructions. "Software" as used herein refers broadly to any type of instructions, whether referred to as software, firmware, middleware, microcode, hardware description language, or otherwise. Instructions may include code (e.g., in source code format, binary code format, executable code format, or any other suitable format of code). The instructions, when executed by one or more processors 230, may cause the processor(s) to perform the various operations and functions described in further detail herein.

Implementations of computing device 200 are not limited to the example embodiment shown in FIG. 2. The number and arrangement of components (210, 220, 230, 240) may be modified and rearranged. Further, while not shown in FIG. 2, computing device 200 may be in electronic communication with other network(s), including the Internet, a local area network, a wide area network, a metro area network, and other networks capable of enabling communication between the elements of the computing architecture. Also, computing device 200 may retrieve data or other information described herein from any source, including storage device 220 as well as from network(s) or other database(s). Further, computing device 200 may include one or more machine-learning models used to implement the neural networks described herein and may retrieve or receive weights or parameters of machine-learning models, training information or training feedback, and/or any other data and information described herein.

Figure 3:
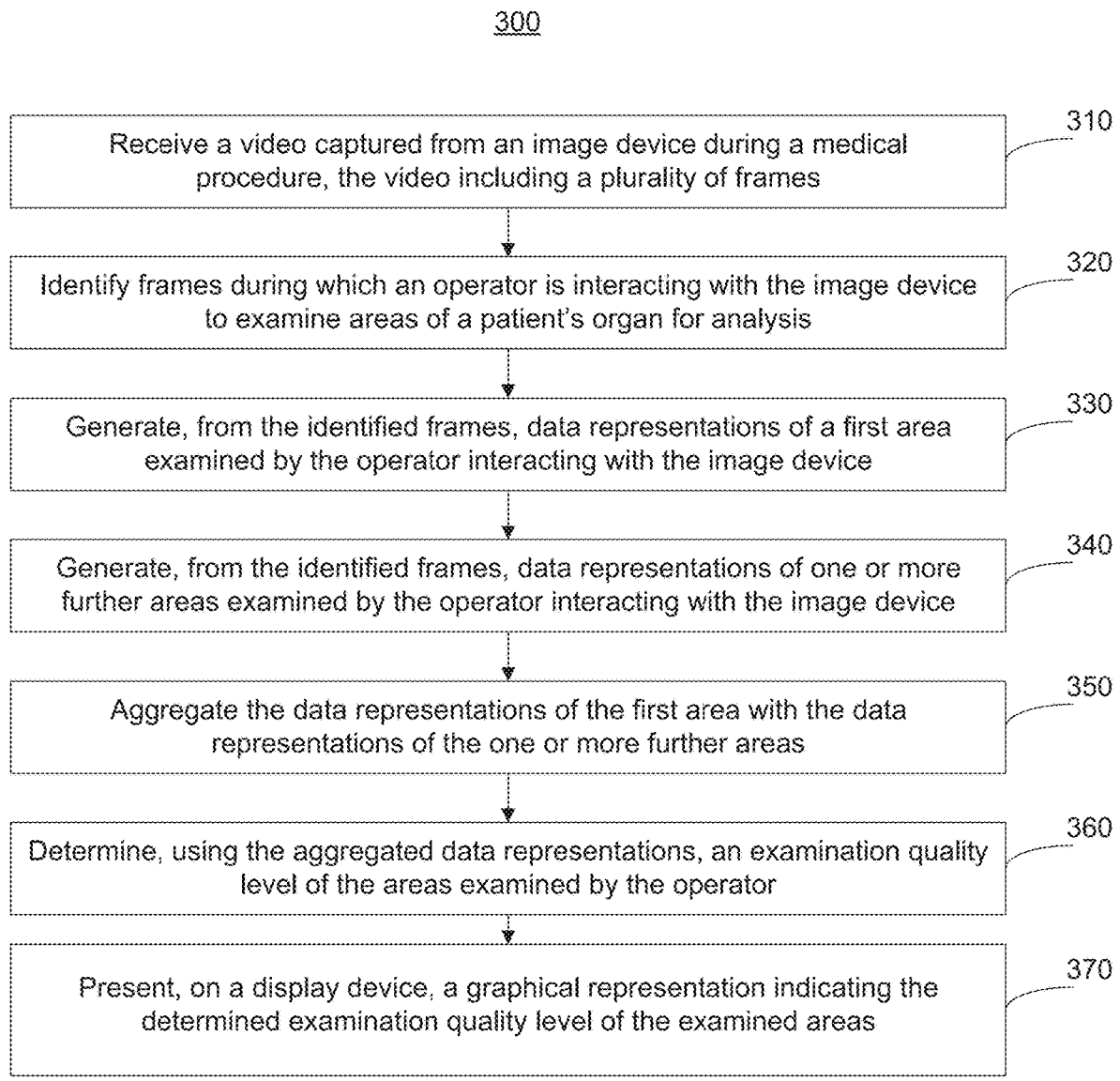
FIG. 3 illustrates an example method for processing video captured during a medical procedure, consistent with embodiments of the present disclosure.

FIG. 3 illustrates an example method 300 for processing video captured during a medical procedure, consistent with embodiments of the present disclosure. The example method 300 may be implemented with the aid of at least one processor (e.g., the at least one processor of computing device 160 or processor(s) 230) or non-transitory computer readable medium, such as a CPU, FPGA, ASIC, or any other processing structure(s) or storage medium of the computing device. As shown in FIG. 3, at step 310, the at least one processor may receive real-time video captured from an image device during a medical procedure on a patient. "Real-time video," as used herein, may refer to video received by the at least one processor, computing device, and/or system without perceptible delay from the video's source (e.g., an image device). For example, the at least one processor may be configured to receive real-time video captured from a medical image device during a medical procedure performed on a patient. A medical image device may be any device capable of producing videos or one or more images of a human body or a portion thereof, such as an endoscopy device, an X-ray machine, a CT machine, or an MRI machine, as described above. A medical procedure may be any action or set of operations performed for examining, determining, detecting, measuring, and/or diagnosing a patient condition. Examples of a medical procedure include an endoscopy, an esophagogastroduodenoscopy, a colonoscopy, a sigmoidoscopy, an endoscopic cholangiopancreatography or an enteroscopy. During the medical procedure, the operator may interact with the image device to examine areas of the patient for analysis. Locations in the human body that an operator may examine for analysis include the rectum, sigmoid colon, descending colon, transverse colon, ascending colon, or cecum. In some embodiments, the medical procedure may include an endoscopic procedure. For example, during an endoscopic procedure, the operator may interact with the image device to examine areas of a colon of the patient to identify objects of interest (e.g., lesions or polyps). It is to be understood, however, that the disclosed systems and methods may be employed in other procedures and applications.

The real-time video received from the image device during a medical procedure may comprise a plurality of frames, consistent with disclosed embodiments. A "frame," as used herein, may refer to any digital representation such as a collection of pixels representing a scene or field of view in the real-time video. In such embodiments, a pixel may represent a discrete element characterized by a value or intensity in a color space (e.g., based on the RGB, RYB, CMY, CMYK, or YUV color models). A frame may be encoded in any appropriate format, such as Joint Photographic Experts Group (JPEG) format, Graphics Interchange Format (GIF), bitmap format, Scalable Vector Graphics (SVG) format, Encapsulated PostScript (EPS) format, or any other format. The term "video" may refer to any digital representation of a scene or area of interest comprised of a plurality of frames in sequence. A video may be encoded in any appropriate format, such as a Moving Picture Experts Group (MPEG) format, a flash video format, an Audio Video Interleave (AVI) format, or any other format. A video, however, need not be encoded, and may more generally include a plurality of frames. The frames may be in any order, including a random order. In some embodiments, a video or plurality of frames may be associated or paired with audio.

The plurality of frames may include representations of an object of interest. An "object of interest," as used herein, may refer to any visual item or feature in the plurality of frames the detection or characterization of which may be desired. For example, an object of interest may be a person, place, entity, feature, area, or any other distinguishable visual item or thing. In embodiments where the plurality of frames comprise images captured from a medical imaging device, for example, an object of interest may include at least one of a formation on or of human tissue, a change in human tissue from one type of cell to another type of cell, an absence of human tissue from a location where the human tissue is expected, or a lesion. Examples of objects of interest in a video captured by an image device may include a polyp (a growth protruding from a gastro-intestinal mucosa), a tumor (a swelling of a part of the body), a bruise (a change from healthy cells to discolored cells), a depression (an absence of human tissue), or an ulcer or abscess (tissue that has suffered damage, i.e., a lesion). Other examples of objects of interest will be apparent from this disclosure.

Referring again to FIG. 3, at step 320, the at least one processor may identify frames from a video received from an image device during a medical procedure performed on a patient (also referred to herein as "real-time video"). During the medical procedure, an operator may interact with the image device to examine areas of an organ of the patient for analysis. An operator's type of interaction with the image device may be determined by analyzing the plurality of frames of video from the image device and classifying frames into one or more of a plurality of actions using, for example, an image classification algorithm or neural network. By way of example, during a medical procedure, an operator may spray water on an area, navigate a camera of the image device to around an intestine or other organ to inspect one or more areas, zoom into an area, inspect a lesion or other formation or object, remove a lesion or other formation or object, perform a biopsy, insert the image device, withdraw the image device, or perform other actions that may aid in the analysis or treatment of a patient. Each frame or group of frames may be classified based on the action(s) performed by the operator. As non-limiting examples, a frame or group of frames may be classified as "spraying" when a stream or burst of water is detected in the frame(s); frame(s) may be classified as "removal" when a surgical instrument is detected in the frame(s); frame(s) may be classified as "inspection" when the area of an object in the frame(s) is determined to be large, thereby indicating that the operator has zoomed in to analyze the object; and/or frame(s) may be classified as "exploration" when it is determined that the view in the frame(s) is substantially along the axis of the patient's body organ, thereby indicating that the operator is moving forward (or backward) into the organ. The classification of frames into one or more of the actions may indicate that the operator is interacting with the image device to examine areas of the patient for analysis. For example, frames classified as "inspection" or "exploration" may be identified as frames in which the operator is interacting with the image device to examine areas of the patient for analysis, as those actions may indicate that the operator is navigating the patient's organ(s) or other body portion(s) to identify objects of interest. Conversely, frames classified as "spraying" or "removal" may be identified as frames in which the operator is not interacting with the image device to examine areas of the patient for analysis, as those actions may indicate that the operator is performing other actions and not navigating the patient's organ(s) or other body portion(s) to identify objects of interest. Classifications may be represented and determined in any form, such as numerical categories (e.g., "1" for exploration, "2" for inspection, "0" for no classification, etc.), alphanumerical categories (e.g., "exploration," "removal," "N/A," etc.), or any other format. It is to be understood that any suitable classification or context may be used to categorize one or more frames and/or to determine that the operator is interacting with the image device to examine areas of the patient for analysis, and the above-described examples are merely illustrative and do not limit embodiments consistent with the present disclosure.

In some embodiments, a neural network may be adapted to perform a contextual evaluation to identify frames among the plurality of frames during which the operator is interacting with the image device to examine areas of an organ of the patient for analysis. For example, the plurality of frames may be fed to one or more neural networks (e.g., a deep neural network, a convolutional neural network, a recursive neural network, etc.), a random forest, a support vector machine, or any other suitable model, as described above, trained to classify the plurality of frames. The neural network may be trained using a plurality of training frames or portions thereof labeled based on one of more action classifications. For example, a first set of training frames (or portions of frames) where an operator is performing an action (e.g., spraying water onto an area), may be labeled as that action (e.g., "spraying"), and a second set of training frames (or portions of frames) where the operator is not performing that action (e.g., "not spraying") or is performing another action altogether (e.g., "exploring") may be labeled accordingly. Other labeling conventions could be used both in binary (e.g., "inspecting" vs "not inspecting") and in multiple classes (e.g., "inspecting" vs "removing" vs "spraying"). Weights or other parameters of the neural network may be adjusted based on its output with respect to a third, non-labeled set of training frames (or portions of frames) until a convergence or other metric is achieved, and the process may be repeated with additional training frames (or portions thereof) or with live data, as described herein.

Machine learning algorithms, models, or weights may be stored in the computing device and/or system, or they may be fetched from a network or database prior to processing. In some embodiments, a machine learning network or algorithm may be re-trained based on one or more of its outputs, such as correct or incorrect classification outputs. The feedback for re-training may be generated automatically by the system or the computing device, or it may be manually inputted by the operator or another user (e.g., through a mouse or keyboard or other input device). Weights or other parameters of the machine learning network or algorithm may be adjusted based on the feedback. In addition, conventional non-machine learning classification algorithms may be used, either alone or in combination with the machine learning classification networks or algorithms, to classify the plurality of frames.

In some embodiments, information specifying the identified operator actions and/or the determination of whether the operator is interacting with the image device to examine areas of the patient may be presented for display in any suitable graphical representation. Such information may indicate when the identified operator actions occur and be presented in real-time on, for example, a display device. The information may also be gathered and updated over time (e.g., during the course of a medical procedure) and the accumulated amount for each action may be presented on a display device. For example, a pie chart may be presented together with labels and/or numbers indicating the percentage of frames (e.g., since the beginning of the medical procedure) corresponding to the determinations, such as "exploring 35%" when thirty-five percent of the plurality of frames are identified as frames in which the operator moved from one area to another, and "removing 20%" when twenty percent of the plurality of frames are identified as frames in which the operator removed a polyp or other object of interest. Other types of graphical displays and representations may be used, such as other types of charts (e.g., a bar graph), alphanumerical characters (e.g., only the labels and/or the percentages), symbols (e.g., a water drop icon to indicate spraying), videos or animated images (e.g., a video of a removal), and/or any other visual representation.

At step 330 in FIG. 3, the at least one processor may generate, from the identified frames, data representations of a first area examined by the operator interacting with the image device. A data representation of an area may be expressed as two-dimensional information (e.g., as planar information on a coordinate system defined by x and y coordinates), as three-dimensional information (e.g., as point cloud information on a coordinate system defined by x, y, and z coordinates), or a combination of both. For example, the data representation may be generated by computing spatial characteristics in and around the view in a frame, such as depth, pose, and edges, although any other visual attributes may be used to generate the data representations.

Depth, for example, may be determined by calculating the disparity between corresponding image points in two frames. For example, in embodiments that comprise two or more cameras, depth may be computed according to the following formula:

$$z = \frac{f * b}{x_1 - x_2}$$

where z is the depth, f is the focal length (i.e., the distance between the image device's lens and its capture sensor), b is the baseline distance (i.e., the distance between the capture points of the first frame and the second frame), $x_1$ is the corresponding point in the first frame, and $x_2$ is the corresponding point in the second frame. As another example, in embodiments that comprise a single or monocular camera, one or more neural networks may be trained to perform monocular depth estimation. The one or more neural networks, for example, may be trained using a deep learning approach, whereby the one or more neural networks are trained using a database or storage device containing a set of image frames with calculated depth information. The neural networks may be retrained based on their output. The one or more neural networks may be paired with other image-processing algorithms, such as edge detection, noise reduction, morphological operations, smoothing algorithms, and any other visual-based processing. The depth estimation using one or more neural networks may be performed on two adjacent frames captured in sequence, two frames captured out of sequence from one another (e.g., one or more frames may be skipped), two frames picked according to a rule (e.g., two frames having the highest quality out a group of frames), randomly, or a combination thereof. Other algorithms and methods for calculating or estimating depth may be used, however, as will be appreciated from those skilled in the art from reviewing this disclosure.

A pose may also be calculated, using any suitable algorithm for determining the location and/or rotation of the image device with respect to a coordinate system. In some embodiments, pose may be estimated using one or more neural networks trained to estimate the relative displacement of the camera from two or more image frames, which may be used as a proxy for the camera's pose. In some embodiments, such neural networks may utilize depth information for each frame in order to determine the camera's relative displacement. Further, a loss function or another optimization approach may be used to ensure consistent scaling in the determined displacement across multiple frames. The neural networks may be applied to consecutive image frames (although in some embodiments, some frames may be skipped), and the results may be stored during the entire procedure or a portion thereof, so as to allow for tracking of the camera's pose at any point in the procedure. For instance, the pose of the camera at a given time with respect to an initial time (e.g., time zero) may be obtained by concatenating relative displacements calculated for each frame pair. The concatenation may be further refined using, for example, optimization algorithms, smoothing operations, or any other suitable refinement process. Other methods for calculating or estimating pose may be used, however, as will be appreciated by those skilled in the art reviewing this disclosure.

Edges of the surfaces in a frame may also be identified. Edges may be determined using any suitable edge detection algorithm (e.g., the Canny method, the Sobel method, differential methods, convolutional methods, or any other methods). For example, in embodiments where the frame is captured during an endoscopy, fold edges in a patient's colon may be detected so as to segment the surfaces depicted in the frame. The detected edges and/or the areas defined by the edges may subsequently be used to generate data representations of areas examined by the operator during the medical procedure. Moreover, the edges and/or the areas defined by the edges may be used during presentation of feedback for the operator. For example, graphical representations of the operator's navigations may be separated or otherwise segmented using edge and/or area information, as further described herein. Accordingly, it is to be understood that visual attributes used to generate the data representations of areas examined by the operator may be used for other purposes, such as feedback to the operator. Further, the types of visual attributes listed above are provided for illustration purposes only and are not intended to be exhaustive.

Consistent with the above description, spatial characteristics, such as depth, pose, and edges, may be determined using one or more machine learning networks. For example, one or more neural networks may be trained to regress depth, pose, and/or edges directly from a single frame from visual features via supervised learning, by minimizing a regression loss. As another example, one or more neural networks may be trained to predict disparities/depth and/or pose from two or more frames, either in a supervised (e.g., with manual verifications) or unsupervised (e.g., with a spatial transformer network) manner. The machine learning networks may be re-trained based on one or more outputs, such as correct or incorrect depth, pose, or edge calculations. The feedback for re-training may be generated automatically by the system or the computing device, or it may be manually inputted by the operator or another user (e.g., through a mouse or keyboard or other input device). Weights or other parameters of the machine learning networks may be adjusted based on the feedback. In addition, conventional non-machine learning algorithms may be used, either alone or in combination with the machine learning networks or algorithms, to determine spatial characteristics, such as depth, pose, and/or edges, in a frame.

Moreover, calculated spatial characteristics may be further refined after calculation. For example, a visual odometry algorithm may be applied to refine a pose estimation after calculation. The visual odometry algorithm may be used to estimate the change in position of the image device over time over multiple frames. The visual odometry algorithm may include pre-processing steps (e.g., distortion removal, etc.), although in some embodiments no pre-processing may be required. A correlation between corresponding visual features in two or more frames may be calculated. A motion flow or pattern may subsequently be estimated based on the correlations (e.g., using the Lucas-Kanade method, the Horn-Schunck method, the Buxton-Buxton method, the Black-Jepson method, or any other method). Other refinements may be applied depending on the specific spatial characteristics calculated or any other information.

Referring again to the example method of FIG. 3, at step 340, the at least one processor may generate, from the identified frames, data representations of one or more further areas examined by the operator interacting with the image device. The data representations of one or more further areas examined by the operator may be generated in the same or a similar manner as for the first area examined by the operator, as discussed above (e.g., by computing spatial characteristics in and around the view in a frame, such as depth, pose, and edges, although other visual attributes may be used to generate the data representations). The first area and the one or more further areas examined by the operator need not be adjacent or examined in sequence, but may rather represent different areas of the patient's body and may be examined at different times during the medical procedure.

At step 350, the at least one processor may aggregate data representations of a first area with data representations of one or more further areas. Multiple data representations may be aggregated by joining representations that are adjacent to one another in the areas examined by the operator. For example, two adjacent data representations may be aggregated into a single data representation using two-dimensional data, three-dimensional data, or both. An example method for aggregating data representations using three-dimensional data of examined areas is described below with reference to FIG. 4. The aggregation may be performed using the coordinate system used to define the data representations, such as an x, y, and z coordinate system. For example, two data representations with one or more overlapping points having the same x, y, and z coordinate may be aggregated using those overlapping points as reference. In some embodiments, an interpolation or a filling algorithm may be performed when the data representations contain missing or corrupted data leading to "holes" in the data representations, so as to create a single seamless data representation by removing such holes. Further, in some embodiments, a distance threshold or other criteria may be applied to determine whether two or more data representations are sufficiently close to one another in a coordinate space to warrant aggregation. It will be appreciated that data representations need not be aggregated into a single data representation but may rather be calculated and stored as multiple separate data representations.

At step 360 of FIG. 3, the at least one processor may determine, using the aggregated data representations, an examination quality level of the areas examined by the operator. An "examination quality level," as used herein, may refer to a quality of an operator's examination of an area captured by the image device. An examination quality level may be determined using the aggregated data representations, such as by calculating a ratio between the areas examined by the operator and an area of a model surface. An examination quality level may also be determined using information associated with the image device, the captured real-time video or frames, or other information, such as the trajectory of the image device, the speed of the image device, as well as other information available to or generated by the computing device. In still further embodiments, an examination quality is determined based on one or more of the following factors or information: (i) the timing of or related to an examination or medical procedure, such as a withdrawal from a location or area of a body organ (such as a base of the cecum) being greater than or equal to a threshold time (such as 6 minutes); (ii) colonoscopy withdrawal time (CWT) statistics related to actions performed by the endoscopists or operator that are computed by, e.g., a context analyzer (see, e.g., WO 2021/156159 A1, titled "Systems and Methods for Contextual Image Analysis," the disclosure of which is expressly incorporated herein) with the CWT statistics being compared to one or more thresholds; trajectory; instantaneous speed; speed statistics; and aggregated data representations of the colon or other organ surface with information about which portions (such as the intestinal mucosa) have been exposed and at which angle and/or distance. The above factors or information are not exclusive but complimentary and may be reviewed in combination to determine the examination quality level.

In some embodiments, an examination quality level may be a quality level of an examination during a medical procedure that is determined from an exposure level. For example, to determine a level of surface exposure (i.e., an "exposure level"), a ratio between the areas examined by the operator and an area of a model surface may be calculated. A "model surface," as used herein, may refer to a representation of a thing or object being examined by the operator, such as a two-dimensional or a three-dimensional model. For example, in embodiments where the operator conducts an examination with an endoscopy, the model surface may be a model of a patient's colon. Following this example, the model surface may comprise a series of cylinders of varying diameters arranged in the shape of a colon. Using the model surface, a ratio between the areas examined by the operator and an area of the model surface may be calculated to indicate the level of exposure. For example, the area of a two-dimensional data representation of a surface captured in one or more frames may be compared with the area of a corresponding two-dimensional area surface in the model surface. As another example, the surface of a three-dimensional data representation of a surface captured in one or more frames may be compared with the surface of a corresponding three-dimensional surface in the model surface. To determine the level of surface exposure, a ratio may thus be calculated based on the comparison, which may be expressed in any desired format (e.g., 25% surface examined, 45% surface examined, etc.).

By way of example, to determine the exposure level with the at least one processor, a cylindrical projection may be performed in which the estimated three-dimensional data representation of the captured surface and a three-dimensional model of the colon are projected in two dimensions. The three-dimensional model of the colon may be generated by one or more methods, such as (i) by applying self-supervised depth estimation algorithm based on monocular video and enforcing frame to frame consistency; (ii) collecting three-dimensional data using three-dimensional sensors (e.g., active stereo or stereo cameras) on a colon or via ex-vivo measurements; and (iii) creating a three-dimensional synthetic dataset including colon shape, colon deformations, colon texture and so forth, where the synthetic colon model is created by, for example, a graphic designer as a sketch or in a parametric fashion with parameter fitting and/or estimation to provide a large dataset. The projection axis may be estimated from the three-dimensional colon model and the three-dimensional reconstructed model. The three-dimensional reconstructed model may be aligned to the three-dimensional colon model using a conventional algorithm such as an iterative closest points (ICP) algorithm. In some embodiments, the projection to the two-dimensions may be done sequentially or simultaneously, based on the shape of the patient's colon or an estimation thereof. Once the projection of the three-dimensional colon model and the three-dimensional reconstructed model are available, the area of the two projections may be compared. In some embodiments, the cylindrical projection approach may not require a colon model. In such cases, the cylindrical projection may be applied to the three-dimensional reconstructed model and the exposed area may be compared against the whole cylinder.

In some embodiments, a ground truth three-dimensional colon reconstruction model may be used to estimate the amount of surface examination from a three-dimensional representation. The model may be trained, tested, and validated before it is used for examination quality level analysis during medical procedures. In some embodiments, the ground truth three-dimensional colon reconstruction model may be generated based on a state-of-the-art depth from a monocular view system. While the accuracy of the three-dimensional model generated using this technique may be high, this technique may be resource-intensive. Alternatively, in some embodiments, the ground truth three-dimensional colon reconstruction model may be generated by using a depth sensor and comparing the reconstruction from the depth data with the reconstruction from the standard color frame data. In still other embodiments, the ground truth three-dimensional colon reconstruction model may be generated based on a synthetic model and using a graphic rendering tool to generate a video sequence. Once the video sequence is generated, a three-dimensional reconstruction algorithm may be performed to the video sequence and the results may be compared with the created synthetic model.

In some embodiments, at least one three-dimensional colon model may be used to estimate the amount of exposed surface from the generated three-dimensional representation(s). In some embodiments, one or more three-dimensional colon models may be provided and a specific model among these models may be selected and compared with the three-dimensional representation(s) based on the completeness of the three-dimensional representation(s). By way of example, if a single long-term three-dimensional representation with no unmerged short-term representations is available, it may be compared with the a colon model in a database of standard colon models. If the long-term representation(s) partially cover(s) one or more portions of the colon, the long-term representation(s) may be compared with a database of one or more portions of the colon such as a segment, a cecum, or ascending colon, to estimate the amount of exposure of a patient's colon surface. In some embodiments, the system may generate multiple short-term representations or a combination of long-term representations and some unmerged short-term representations. In such cases, a cylindrical projection approach may be employed to determine an appropriate fit for the available partial short-term and long-term representations.

In other embodiments, the exposure may be measured by directly projecting the three-dimensional reconstructed model onto the three-dimensional colon model surface. In such cases, each three-dimensional vertex or three-dimensional face of the three-dimensional reconstructed model may be projected onto the three-dimensional colon model. The exposure level may be determined from the ratio between the area of the three-dimensional colon model matched with the projected points or vertices and the total area of the three-dimensional model surface.

From patient to patient, there may be differences in terms of the physical dimensions and characteristics of the patient's intestines. However, intestines have a common anatomical structure and set of landmarks (flexures, valve, orifice, etc) across patients. These common characteristics and landmarks can be used to build a canonical model of the intestine. Such models can provide a sufficient level of accuracy to localize a mucosa area within the patient's colon. Further, any differences can be addressed by the systems and methods of the present disclosure through training on data from a variety of patients. Alternatively, or additionally, information related to a patient's colon (e.g., shape, size, and other characteristics) may be used to select, as part of a best fit operation, one among a plurality of colon models or it may be used to make adjustments to a base colon model.

Embodiments of the present disclosure may also be configured to address differences between different endoscopic cameras. This may be done to minimize any influences on the collected image data and determined exposure level. For example, one or more camera calibration methods may be applied. In some embodiments, a monocular depth estimation approach is improved by applying an intrinsic camera calibration, which may be performed at least once for each image device at, for example, the time of installation and/or before every medical procedure. More advanced algorithms can deal with uncalibrated cameras, providing an estimation of the camera parameters in the convolutional neural network output. See, e.g., «https://openaccess.thecvf.com/content_ICCV_2019/papers/Gordon_Depth_From_Videos_in_the_Wild_Unsupervised_Monocular_Depth_Learning_ICV_2019_paper.pdf».

In some embodiments, an examination quality level may be a quality level of an examination during a medical procedure that is determined from a trajectory of the image device. A trajectory of the image device may be determined using any suitable trajectory estimation algorithm. For example, corresponding points in two or more frames may be identified. The identified corresponding points may subsequently be translated into coordinates in a pre-defined coordinate system (e.g., a coordinate system having x, y, and z coordinates). A rotation matrix and a translation vector describing the rotation and translation, respectively, of the two or more frames may then be calculated using the translated coordinates. A fitting algorithm, such as Random Sample Consensus (RANSAC), Maximum Likelihood Estimator Sample Consensus (MLESAC), PEARL, Hough, Least Squares Fitting, or any other fitting algorithm, may subsequently be applied to find the best rotation matrix and translation vector by ignoring outlier points. The computed rotation matrix and translation vector may subsequently be converted to the coordinate system to compute a trajectory of the image device with respect to a starting point (e.g., a first frame). The above process may be repeated with respect to multiple other frames of the real-time video so as to create a trajectory of the image device during a portion of the real-time video. It is to be understood that other trajectory estimation algorithms may be utilized, however.

In some embodiments, an examination quality level may be a quality level of an examination during a medical procedure that is determined from a speed of the image device. A speed of the image device may be determined using any suitable speed estimation algorithm. For example, after computing the trajectory of the image device as described above, a relative speed between two or more consecutive frames (although some frames may be skipped) may be calculated. The speed may be calculated based on the distance traveled by the image device during its trajectory between two or more frames. As a further example, an accelerometer or a tracking device may be used to determine the speed of the image device as the operator interacts with it during a medical procedure. It is to be understood that other steps or algorithms for estimating speed may be utilized, however.

In some embodiments, an examination quality level may be a quality level of an examination during a medical procedure that is determined using a combination of characteristics. The computing device may determine an examination quality level using, for example, the trajectory of the image device, the speed of the image device, the ratio between the areas examined by the operator and an area of a model surface, and/or any other information available to or generated by the computing device. For example, a high examination quality level may be the result of a good image device trajectory, an appropriate image device speed, and/or a high exposure level (e.g., a high ratio of examined surface with respect to a model surface). Conversely, a low examination quality level may be the result of a bad image device trajectory, an inappropriate image device speed, and/or a low exposure level (e.g., a low ratio of examined surface with respect to a model surface). Generally, a trajectory may be evaluated in terms of its smoothness, regularity, symmetry, and/or any other attribute associated with the trajectory. As an example, for an endoscope, a good image device trajectory should follow a spiral or spiral-like trajectory as opposed to a straight trajectory. Other characteristics of the trajectory may also be check. By way of example, the trajectory of an endoscope camera should minimize the distance from the mucosa, optimize the angle with respect to the mucosa surface such that the direction of observation is normal to the mucosa surface, and/or provide observation of the mucosa behind the colon folds. In some embodiments, the examination quality level may be a qualitative binary value. Some examples of qualitative binary values include: good or bad; low or high; acceptable or unacceptable; and fail or pass. In some embodiments, the examination quality level may be a numerical value, such as a score on a continuous scale (e.g., a score on a scale such as from 0 to 1, 1 to 10, or 1 to 100).

In some embodiments, the examination quality level may be determined based on a threshold value of the total area exposed. As an example, the examination quality level may be deemed high or good if the total area of the organ exposed is 50% or more. However, if the total area of the organ exposed is less than 50%, the examination quality level may be deemed low or bad. It will be appreciated that other thresholds may be used and other ways of expressing the examination quality level (e.g., pass or fail) may be implemented.

In some embodiments, the trajectory is determined based on an estimation of camera pose in consecutive frames. As disclosed herein, for an endoscope camera, the trajectory should maximize the visibility of areas behind the colon folds and optimize the direction of observation and distance from the mucosa surface. A spiral like trajectory (bottom) is preferrable to a straight-line trajectory. In some embodiments, a more accurate trajectory evaluation is achieved by analyzing the aggregate field of view of the camera while moving along its trajectory In some embodiments, an examination quality level may be determined based on the speed of the image device alone or in combination with other factors or information. For example, speed may be considered as optimal when it is within predefined speed limits recommended by guidelines for minimum procedural timings, and/or when it is smooth and constant (e.g., there are no excessive peaks and/or dips in speed). Additionally, or alternatively, speed of the image device may be considered optimal when it allows clear observation of the mucosa surface. In some embodiments, the combination of a good image device trajectory and optimum image device speed may be desirable and result in a determination of a high examination quality level. As a further example, the examination quality level may be determined to be low if the image device is moving along a good trajectory but at a higher-than-optimal speed such that the mucosa surface is not adequately or clearly imaged. In some embodiments, an examination quality level may be determined based on surface exposure alone or in combination with other factors or information. For example, exposure may be considered adequate when the ratio of examined surface with respect to a model surface is within a predetermined exposure range, and which may be based on the local or short-term exposure and/or the global or long-term exposure. As used herein, "exposure" refers to the ratio of observed colon surface area to the total colon surface area. In still further embodiments, one or more analyzed factors such as trajectory, speed, and/or exposure may be used to determine the examination quality level. Other analyzed values or calculations may be used to determine the examination quality level, however, as explained above.

In some embodiments, the at least one processor may be further configured to determine the examination quality level on a real-time basis during the medical procedure and update the determined examination quality level as the medical procedure is performed on the patient. For example, a predetermined time interval may be used to periodically update the examination quality level during the medical procedure (e.g., every millisecond(s), every second(s), every minute(s), every hour(s), etc.) or at random intervals that may be within a specified time period. As another example, the examination quality level may be updated based on the amount of area examined by the operator (e.g., the examination quality level may be updated every few centimeters or inches examined), the distance traveled by the image device (e.g., the examination quality level may be updated every few centimeters or inches traveled), and/or other suitable interval or underlying variable. As a further example, the examination quality level may be updated based on an action performed by the at least one processor of the computing device, such as after generating a data representation of an area examined by the operator, after aggregating data representations, or after any other operation performed by the at least one processor. The examples provided above are illustrative only and are not intended to be exhaustive.

Figures 12A, 12B:
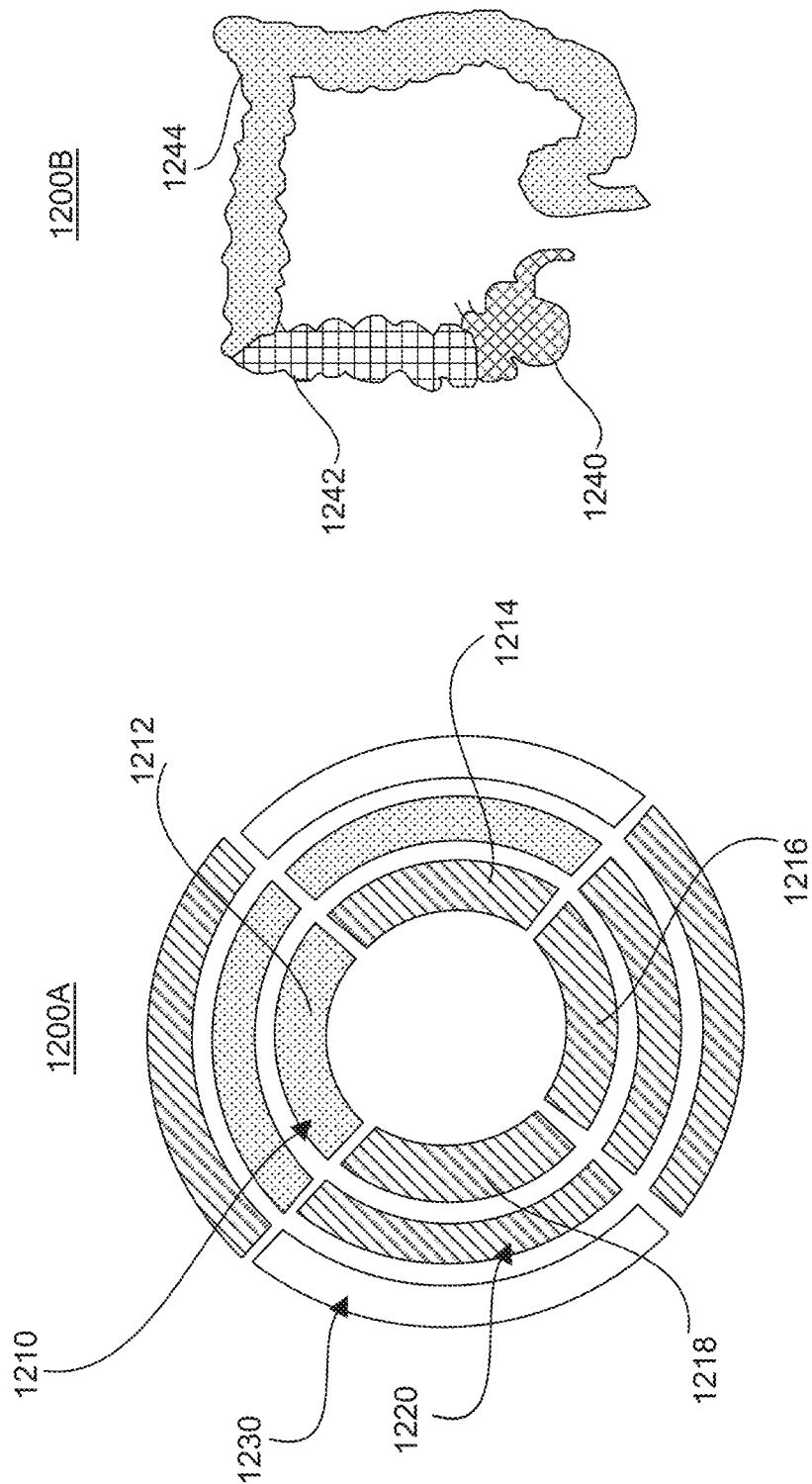
FIGS. 12A and 12B illustrate examples of graphical representations for indicating examination quality levels and/or other attributes of the operator's navigation, consistent with embodiments of the present disclosure.

At step 370 of the example method of FIG. 3, the at least one processor may present, on a display device during the medical procedure, a graphical representation indicating the examination quality level of the areas examined by the operator. The display device, such as display device 180 described above in connection with FIG. 1, may be an LCD display, virtual reality display, augmented reality display, etc. The examination quality level may be presented in any desired format, such as percentage values, classification labels, alphanumeric characters, colors, images, videos, graphs, or any other format. For example, the examination quality level may be presented as a plurality of areas corresponding to areas examined by the operator during a medical procedure, and which may be presented as different colors depending on the examination quality level (e.g., green for a high examination quality level, and red for a low examination quality level). As a further example, a percentage value or a exposure classification may be displayed indicating the examination quality level, such as "25% Exposure" or "Low Exposure" when the computing device determines that only twenty-five percent of the areas of the surface have been examined by the operator during the medical procedure or a portion of the medical procedure (e.g., during the last section of a surface, the last minute(s), the entire medical procedure, etc.). As a further example, a two-dimensional or three-dimensional model having one or more sections may be displayed to the operator indicating the examination quality level for each section (e.g., a green section for a high examination quality level, and red section for a low examination quality level). As yet another example, the graphical representation may indicate a ratio between the areas examined by the operator and an area of a model surface and/or non-examined areas, which may be expressed as a percentage, value, classification, or any other suitable format. Further example graphical representations for presenting an examination quality level or value are illustrated in FIGS. 12A and 12B. These examples may be modified to include other information, such as speed and/or trajectory information (see, e.g., FIGS. 5A and 5B). Other graphical representations may be used, however, as will be appreciated from this disclosure.

In some embodiments, the at least one processor may be further configured to modify the graphical representation as the determined examination quality level is updated during the medical procedure. As non-limiting examples, the at least one processor may be configured to modify at least one of a color, a pattern, an image, a video, and/or an alphanumeric character of the graphical representation. For example, in embodiments where the examination quality level is presented as a plurality of areas corresponding to areas examined by the operator, the color of the areas may change depending on change in the examination quality level (e.g., changing from green to red to indicate a change from a high to a low examination quality level, or changing from red to green to indicate a change from a low to a high examination quality level). As a further example, in embodiments where the examination quality level is presented as a percentage value or a exposure classification, the percentage or classification may change depending on the change in examination quality level (e.g., changing from "25% Examination Quality Level" to "50% Examination Quality Level" to indicate an increase of examination quality level from twenty-five percent to fifty percent, or changing from "Low Examination Quality Level" to "High Examination Quality Level" to indicate an increase from a low to a high examination quality level). As yet another example, in embodiments where the examination quality level is presented as a two-dimensional or three-dimensional model having one or more sections, a visual attribute of the model may change depending on the change in examination quality level (e.g., a section may change from green to red to indicate a decrease in examination quality level from a high to a low examination quality level, or a section may change from red to green to indicate an increase in examination quality level from a low to a high examination quality level). Other modifications to the graphical representation may be used to indicate a change in the exposure, however, as will be appreciated from this disclosure.

Figure 4:
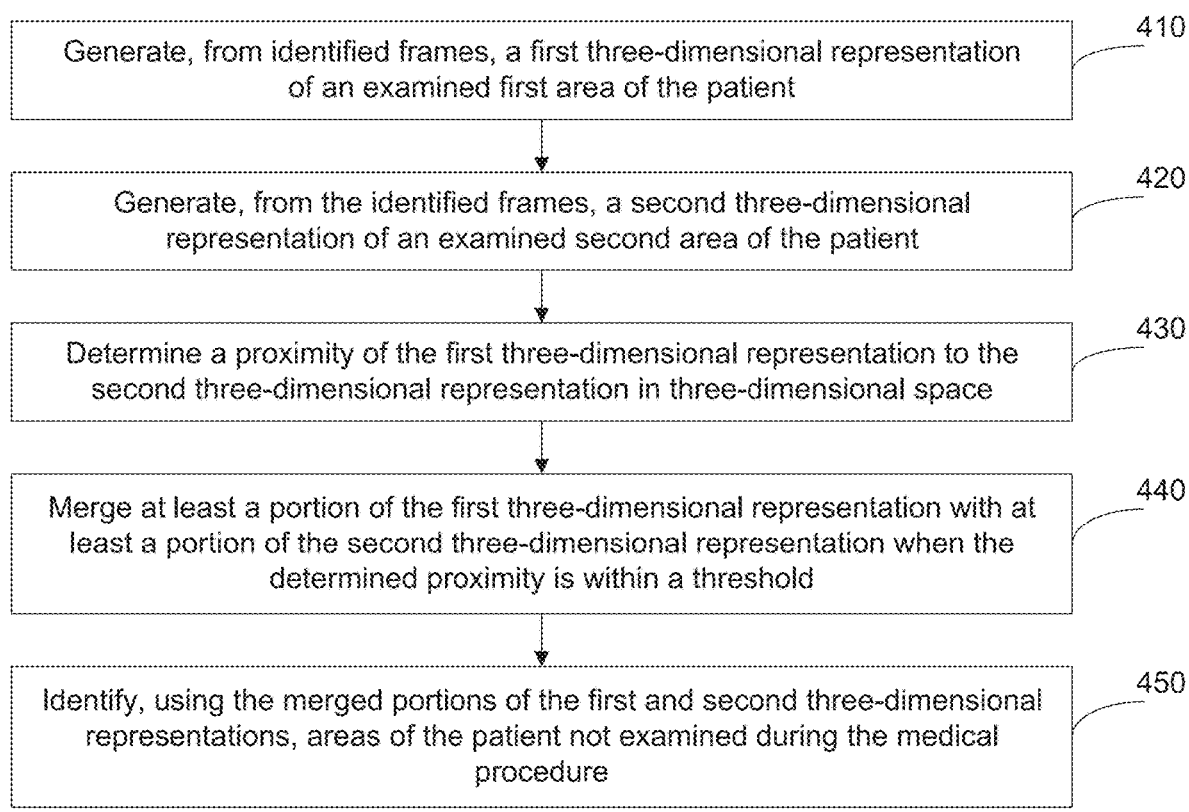
FIG. 4 illustrates an example method for generating a three-dimensional representation of examined areas, consistent with embodiments of the present disclosure.

FIG. 4 illustrates an example method 400 for generating a three-dimensional representation of examined areas, consistent with embodiments of the present disclosure. Method 400 may be performed on frames identified as the frames during which an operator is interacting with the image device to examine areas of an organ of the patient for analysis. The example method 400 may be implemented with one or more processors, such as the at least one processor of computing device 160 or processor(s) 230 and performed as part of a process for determining an examination quality level or value (see, e.g., the example method of FIG. 3). It will be appreciated that method 400 is a non-limiting example.

As shown in FIG. 4, at step 410 a first three-dimensional representation of an examined first area may be generated, and at step 420 a second three-dimensional representation of an examined second area may be generated, both of which may be in the form of a point cloud in a coordinate system having x, y, and z coordinates. Further, in some embodiments, the generated three-dimensional representation (and/or two-dimensional data) may be used to generate data representations. As discussed above, generating data representations may involve computing spatial characteristics in and around the view in a frame, such as depth, pose, and edges. Subsequently, at step 430, a proximity of the first three-dimensional representation to the second three-dimensional representation in the coordinate system space may be determined. The proximity may be calculated by comparing the coordinates of points along the first and second three-dimensional representations and determining the minimum distance between two of the points. If there is an overlap between the first and second three-dimensional representations, the proximity may be determined to be zero. If there is no overlap, a threshold may be applied to determine whether the proximity falls within a predetermined threshold, which indicates that the first and second three-dimensional representations are sufficiently close with respect to one another in the coordinate system space. If the proximity falls within the threshold, at step 440, at least a portion of the first and second three-dimensional representations may be merged so as to create a single three-dimensional representation. At step 450, areas not examined by the operator may be identified using the merged portions, such as by comparing it with a surface model, as further described herein. Following completion of method 400, an examination quality level using the aggregated three-dimensional representation may be determined, as explained herein.

Each three-dimensional representation may be based on its own coordinates when it is generated. In some embodiments, a merging process may merge two or more three-dimensional representations. By way of example, a merging process may include a merging algorithm executed by at least one processor to bring the two or more three-dimensional representations into a common reference frame. The merging algorithm may use prior information associated with each three-dimensional representation to estimate the initial relative position between the representations. For example, the merging algorithm may use a time difference between the last frame of a three-dimensional representation and the first frame of the succeeding representation. In some embodiments, the merging process may further include executing geometric alignment algorithms such as iterative closest points (ICP) and photometric algorithms. If there is any overlapping found between the first and the second three-dimensional representations, the alignment may be successful. In absence of any overlap, the alignment may be unsuccessful, and a long-term three-dimensional representation may be deemed unavailable.

In some embodiments, the method may include generating short-term representations of an examined area by aggregating multiple three-dimensional representations built from consecutive frames of portions of an organ examined by an operator. The aggregation of multiple three-dimensional representations may be interrupted by factors including, but not limited to, abrupt camera movement, camera focused on water or hitting the mucosa, a trigger from a context evaluation model, failure of an algorithm, among other factors. In the event of an interruption of a first short-term representation from multiple three-dimensional representations, the method may include initializing a second short-term representation from multiple three-dimensional representations may be formed. Following formation of two or more short-term representations, a merging process may be performed, for example by executing a merging algorithm as discussed above, to merge at least two short-term representations to form a long-term representation. In some embodiments, all the short-term representations may be merged to form a long-term representation such that there are no unmerged short-term representations. However, in some embodiments, the merging process may result in formation of a long-term representation and some unmerged short-term representations. The output of the merging process may be used to form a three-dimensional reconstruction model of the examined surface of a patient's organ, such as a colon of the patient.

Further, in some embodiments, an examination quality level may be estimated based on a combination of factors including speed, trajectory of the device, and an estimation of the ratio of mucosal exposure. In some embodiments, the ratio of mucosal exposure may be estimated, for example, as a global score from a weighted average of the exposures based on short-term and long-term representations. In some embodiments, the ratio of mucosal exposure may be estimated based on a comparison of the generated long-term three-dimensional representation and a complete three-dimensional model of a patient's organ.

Figure 5:
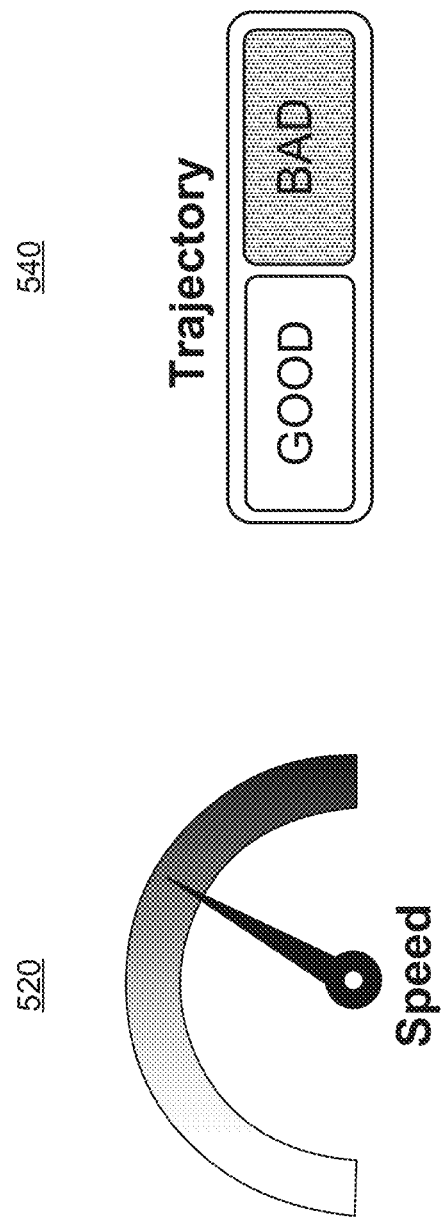
FIGS. 5A and 5B illustrate examples of graphical representations for indicating speed and trajectory information, consistent with embodiments of the present disclosure.

As disclosed herein, information or statistics may be generated and displayed to indicate the quality of the operator's navigation and/or to reflect or determine an examination quality level or value. For example, speed and/or trajectory information may be determined and presented on a display device for an operator (e.g., display 180 in FIG. 1). This information may be displayed separately (e.g., on a separate display or output) or as augmenting information that is overlaid with the real-time video from the image device (e.g., on display 180). In some embodiments, the speed and/or trajectory information may be displayed as part of one or more graphical representations. The graphical representations may be combined and/or include a graphical representation of an examination quality level or value. By way of example, FIGS. 5A and 5B illustrate exemplary graphical representations of speed and trajectory information that may be generated and presented to an operator (e.g., separately or as augmenting information). The exemplary information of FIGS. 5A and 5B may be determined and presented during a medical procedure to provide feedback on the quality of the operator's navigation during the medical procedure. Further, the speed and/or trajectory information may be updated and displayed in real-time during a medical procedure (e.g., at predetermined time intervals) as a result of an operator's actions. Example methods and algorithms for determining speed and trajectory information are described above. Further embodiments are also described below (see, e.g., the example method of FIG. 6).

In FIG. 5A, for example, a graphical representation 520 is shown of the image device's speed. Although depicted in FIG. 5A as a speed dial, speed may be represented in any other suitable format, such as a determined speed (e.g., a "1 mm/sec"), a speed classification (e.g., "fast" or "slow"), an image (e.g., a stop sign to indicate a fast speed), a video or moving image (e.g., a flashing light to indicate a fast or slow speed), or any other suitable format. Further, the speed information may be updated and displayed in real-time during a medical procedure, at predetermined time intervals, as a result of an operator's actions, or at any other time. For example, the speed dial of FIG. 5A may move to the right or the left as the image device's speed increases or decreases, respectively. In FIG. 5B, a graphical representation 540 is shown of the image device's trajectory. Although depicted in FIG. 5B as a binary classification of "GOOD" or "BAD" trajectory, trajectory may be represented in any other suitable format, such as a trajectory line (e.g., as a continuous line in a two-dimensional or three-dimensional representation of a patient's colon), a sliding scale or dial (e.g., a scale similar to the speed dial of FIG. 5A), other classifications (e.g., "VERY GOOD," "VERY POOR," or "AVERAGE"), an image (e.g., a stop sign to indicate a poor trajectory), a video or moving image (e.g., a flashing light to indicate a good or bad trajectory), or any other suitable format. Further, the trajectory representation may be updated in real-time during a medical procedure, at predetermined time intervals, or as a result of an operator's actions. For example, the word "GOOD" in FIG. 5B may be highlighted instead of the word "BAD" when the operator's trajectory changes from an unacceptable level to an acceptable level during the medical procedure.

Figure 6:
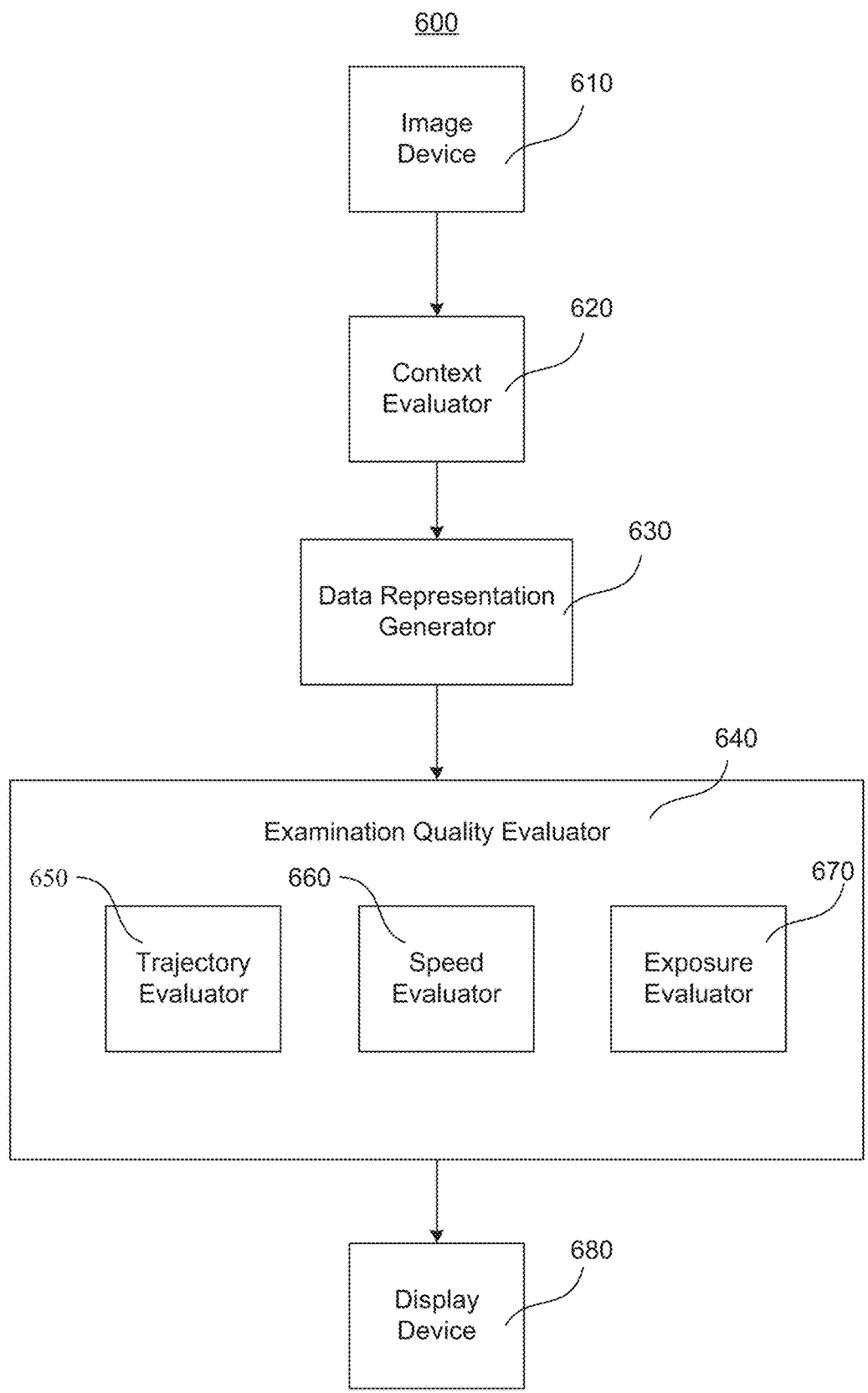
FIG. 6 illustrates an example system for processing frames of a video, consistent with embodiments of the present disclosure.

FIG. 6 illustrates an exemplary system for processing frames of a video, consistent with embodiments of the present disclosure. As shown in FIG. 6, system 600 may comprise an image device 610, a context evaluator 620, a data representation generator 630, an examination quality evaluator 640, and a display device 680. Image device 610 may be the same or similar to image device 140 described above in connection with FIG. 1 (e.g., an endoscopy machine, an X-ray machine, a CT machine, an MRI machine, or any other medical imaging device), and display device 680 may be the same or similar as the display device 180 also described above in connection with FIG. 1 (e.g., an LCD, LED, or OLED display, an augmented reality display, a virtual reality display, or any other suitable display device). Image device 610 may be configured to capture video or real-time video, which in some embodiments may be captured during a medical procedure (e.g., an endoscopic procedure), as described above. Image device 610 may be configured to feed the captured real-time video to context evaluator 620.

Context evaluator 620 may comprise one or more processors that implement one or more machine learning networks or algorithms, conventional algorithms, or a combination of both, as described above. Context evaluator 620 may be configured to identify an operator's type of interaction with image device 610 in one or more frames of the captured video. For example, context evaluator 620 may classify a frame or group of frames of the captured video based on the operator's action in those frame(s), such as spraying water on an area, zooming into an area, inspecting a lesion, removing a lesion, performing a biopsy, performing an insertion of the image device, performing a withdrawal of the image device, or any other action, consistent with the description above. Context evaluator 620 may be further configured to determine whether the operator is interacting with the image device to examine areas of the patient for analysis, based on the identified interaction. The frame(s) identified as those in which the operator is exposing areas may be further processed by system 600, while frame(s) not identified as such may be discarded or ignored by system 600. For example, frames classified as "inspection" or "exploration" may be identified as frames in which the operator is interacting with the image device to examine areas of the patient for analysis, while frames classified as "spraying" or "removal" may not. Context evaluator 620 may feed the former to data representation generator 630 for further processing.

Data representation generator 630 may include one or more processors configured to generate data representations from frames identified by context evaluator 620 as the frames in which the operator is interacting with the image device to examine areas of the patient for analysis. Data representations may be generated based on three-dimensional data, two-dimensional data, or both, as discussed above. Data representation generator 630 may be further configured to aggregate at least a portion of the generated data representations. In some embodiments, a distance threshold or other criteria may be applied to determine whether aggregation is warranted, as described above. Further, in some embodiments, no aggregation may be performed when it is not warranted or needed. Data representation generator 630 may subsequently feed the aggregated (or non-aggregated) data representations to examination quality evaluator 640.

Examination quality evaluator 640 may include one or more processors configured to determine an examination quality level of the areas examined by the operator. The determination may be performed either in a local or short-term basis (e.g., by analyzing areas examined in one or more specific frames), a global or long-term basis (e.g., by analyzing areas examined during an entire medical procedure or a portion thereof), or both. As described above, the examination quality level may be determined based on information associated with the quality of the operator's examination of an area, such as an exposure level determined from a ratio between the areas examined by the operator and an area of a model surface, the trajectory of the image device, the speed of the image device, and/or any other information available to or generated by system 600. As shown in FIG. 6, for example, examination quality evaluator 640 may include one or more computer-implemented components for analyzing specific characteristics of the operator's quality of examination, such as trajectory evaluator 650 for analyzing the image device's trajectory, speed evaluator 660 for analyzing the image device's speed, and exposure evaluator 670 for comparing the areas examined by the operator to an area of a model surface. It is to be understood, however, that examination quality evaluator 640 may include any one or more of these components. Further, examination quality evaluator 640 may comprise other components for analyzing other specific characteristics of the operator's quality of examination other than those shown in FIG. 6, depending on the specific application or context.

Although not shown in FIG. 6, system 600 may comprise one or more computing devices (such as computing device 160) that may include one or more processors configured to modify the video from image device 610 with augmenting information, including one or more graphical representations of the examination quality level or value calculated by examination quality evaluator 640, the trajectory calculated by trajectory evaluator 650, the speed calculated by speed evaluator 660, the ratio or area calculated by exposure evaluator 670, and/or any other desired information. The augmented video may be fed to display device 680 for viewing by the operator of image device 610 and other users during the medical procedure (i.e., in real-time with the medical procedure).

In some embodiments, the examination quality level may be calculated as combination of one or more short-term examination quality levels and one or more long-term examination quality levels. A short-term examination quality level may represent an examination quality level of an area that is being currently examined by the operator. A long-term examination quality level may represent an examination quality level of areas previously examined by the operator during an entire medical procedure or a portion thereof. A short-term examination quality level may be computed in the same or similar manner as described above with respect to the examination quality level, such as by calculating the trajectory of the image device, the speed of the image device, a ratio between the areas examined by the operator and an area of a model surface, and/or any other factors or information available to or generated by the computing device. A long-term examination quality level may be the combination of two or more short-term examination quality levels, and which may be calculated as a sum, average, mean, median, mode, distribution, or any other representation of two or more short-term examination quality levels.

Figure 7:
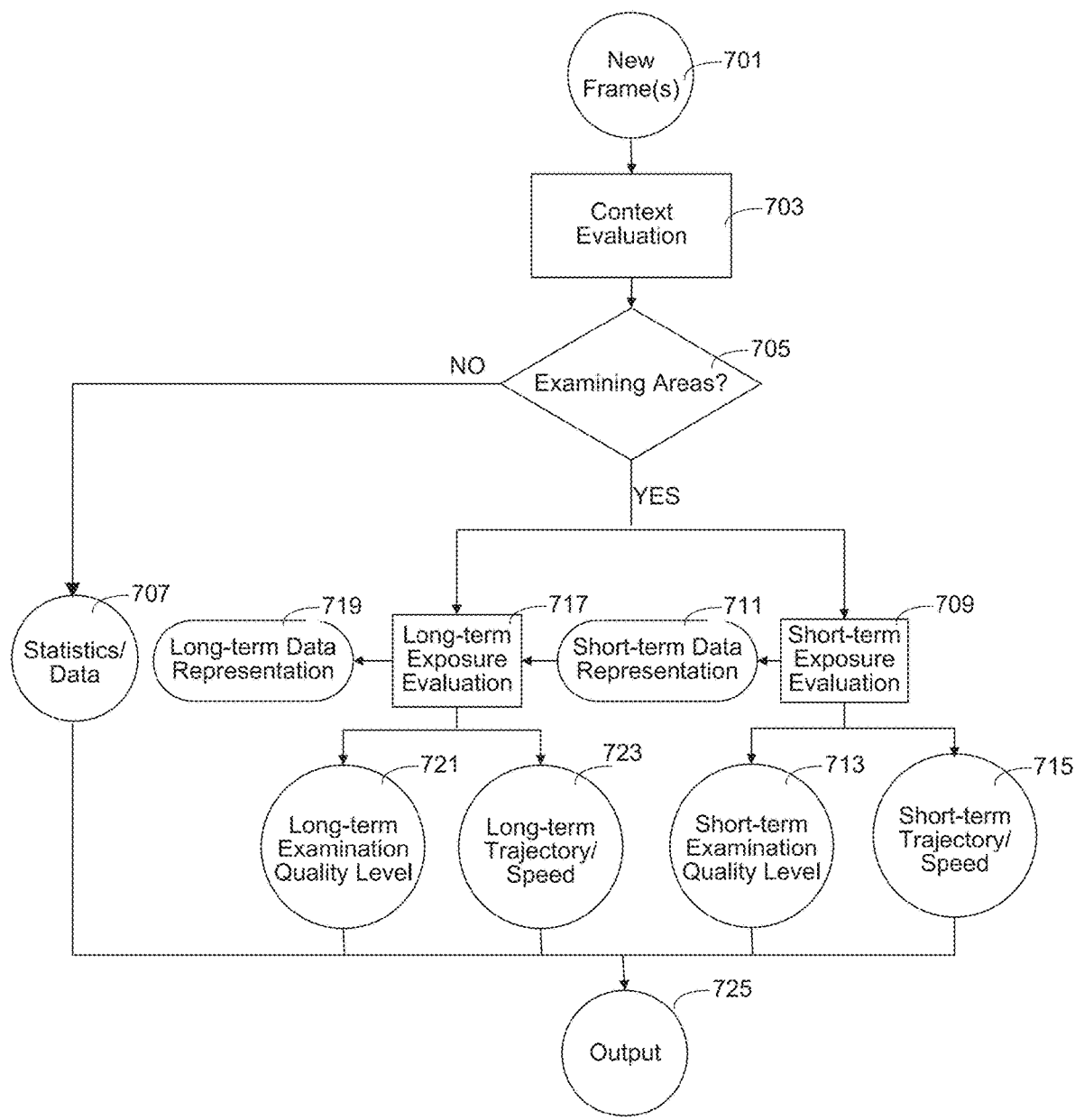
FIG. 7 illustrates an example method for determining short-term and long-term examination quality levels, consistent with embodiments of the present disclosure.

FIG. 7 illustrates an example method 700 for determining short-term and long-term examination quality levels, consistent with embodiments of the present disclosure. The example method 700 may be implemented with at least one processor (e.g., the at least one processor of computing device 160 in FIG. 1 or processor(s) 230 in FIG. 2). It will be appreciated that method 700 is a non-limiting example. As shown in FIG. 7, at step 701 a new frame may be captured (e.g., by image device 140 in FIG. 1) and received by the at least one processor. At step 703, the at least one processor may perform context evaluation to identify an operator's type of interaction with an image device (e.g., image device 140 in FIG. 1) in the frame. For example, the at least one processor may classify frames of the captured video based on the operator's action, such as spraying water on an area, zooming into an area, inspecting a lesion, removing a lesion, performing a biopsy, performing an insertion of the image device, performing a withdrawal of the image device, or any other action, consistent with the description above.

At step 703, the at least one processor may determine whether or not the operator is interacting with the image device to examine areas in the frame, which may be based on the identified action(s). At step 707, if the at least one processor determines that the operator is not interacting with the image device to examine areas in the frame, statistics or other data may be generated based on the at least one processor's analysis of the current frame and/or previous frames. For example, at step 725, the determined statistics or data that may later be presented as a chart, table, or other graphical representation that is displayed or otherwise provided as output. Although not shown in FIG. 7, such a chart, table, or other graphical representation may be presented to the operator together with labels and/or numbers indicating the percentage of frames corresponding to the determinations, such as "exploring 35%" when thirty-five percent of frames are identified as frames in which the operator moved from one area to another, and "removing 20%" when twenty percent of frames are identified as frames in which the operator removed a polyp or other object of interest. In some embodiments, however, no statistics or data may be outputted. In either case, the processing of the frame may end at step 725. If the at least one processor determines that the operator is interacting with the image device to examine areas in the frame, however, processing of the frame may continue at steps 709 and 717.

At step 709, the at least one processor may perform a short-term exposure evaluation of the frame. The short-term exposure evaluation may include generating short-term data representation 711 corresponding to the surface in the frame, which may be based on three-dimensional data, two-dimensional data, or both, as discussed above. The short-term exposure evaluation may also include determining short-term examination quality level 713 corresponding to the quality of the operator's examination of the surface in the frame. The short-term examination quality level may be determined by analyzing the short-term data representation, such as by calculating a ratio between the areas of the short-term data representation and an area of a model surface. As will be appreciated from this disclosure, other ways of determining the short-term level of exposure of surfaces in the frame may be used. As shown in the example method of FIG. 7, the short-term examination quality level may be determined by calculating information associated with the image device at the time the frame was captured, such as short-term trajectory/speed 715. The determined short-term examination quality level 713 and short-term trajectory/speed 715 may be outputted at step 725. Although not shown in FIG. 7, the determined short-term examination quality level 713 and short-term trajectory/speed 715 may be presented to the operator and/or other users using a display device or through any other means.

At step 717, the at least one processor may perform a long-term exposure evaluation of the frame. The long-term exposure evaluation may include aggregating short-term data representation 711 with other previously generated data representations into long-term data representation 719, which may be based on three-dimensional data, two-dimensional data, or both, as discussed above. The long-term exposure evaluation may also include determining long-term estimation quality level 721 corresponding to the quality of the operator's examination of surfaces during the entire medical procedure or a portion thereof. The long-term estimation quality level may be determined by analyzing the long-term data representation, such as by calculating a ratio between the areas of the long-term data representation and an area of a model surface. As will be appreciated from this disclosure, other ways of determining the long-term level of exposure of surfaces during the entire medical procedure or a portion thereof may be used. As further shown in FIG. 7, the long-term examination quality level may be determined by calculating information associated with the image device during the entire medical procedure or a portion thereof, such as long-term trajectory/speed 723. The determined long-term examination quality level 721 and long-term trajectory/speed 723 may be displayed or otherwise provided as output at step 725. Although not shown in FIG. 7, the determined long-term examination quality level 721 and long-term trajectory/speed 723 may be presented to the operator and/or other users using a display device or through any other means.

Figure 8:
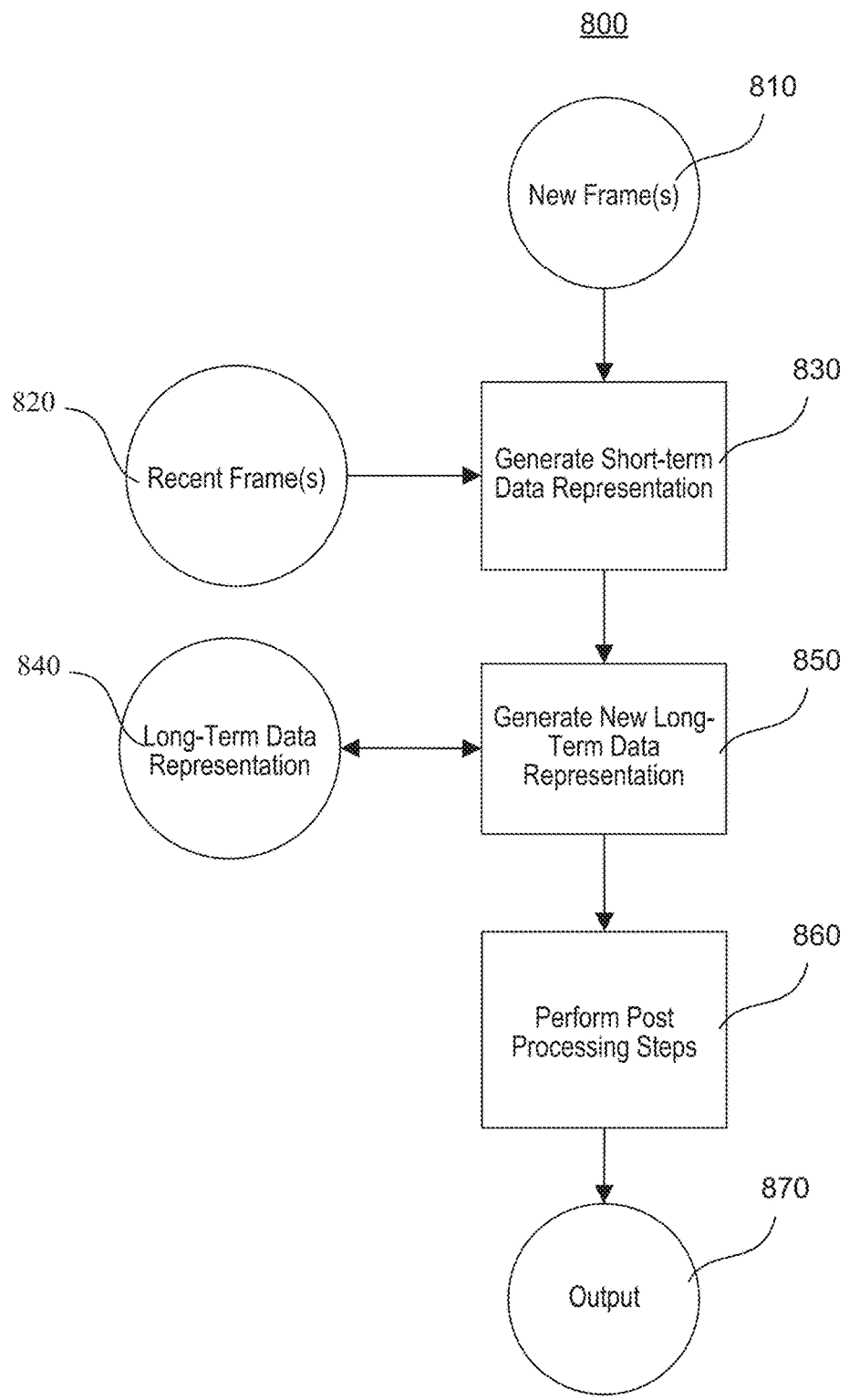
FIG. 8 illustrates an example method for generating short-term and long-term data representations, consistent with embodiments of the present disclosure.

FIG. 8 illustrates an example method 800 for generating short-term and long-term data representations, consistent with embodiments of the present disclosure. Method 800 may be performed on frames identified as the frames in which an operator is interacting with the image device to examine areas of an organ of the patient for analysis (e.g., as described in connection with method 700 of FIG. 7). Concurrently with or following method 800, short-term and long-term evaluations may be performed to determine short-term and long-term examination quality levels, respectively, as described herein. The example method 800 may be implemented with one or more processors (e.g., the at least one processor of computing device 160 in FIG. 1 or processor(s) 230 in FIG. 2). It will be appreciated that FIG. 8 is a non-limiting example and that modifications may be made to method 800, including by adding, removing, modifying and/or reordering the steps illustrated and described herein.

As shown in FIG. 8, at step 810 a new frame may be received by at least one processor (e.g., the at least one processor of computing device 160 in FIG. 1 or processor(s) 230 in FIG. 2). At steps 820, one or more previously captured frames may optionally also be received by the at least one processor for processing in step 830. The previously captured frames may be stored and retrieved from a memory, database, or buffer, for example. In some embodiments, however, processing may be performed on a frame-by-frame basis without processing previously captured frames together with the newly captured frame. At step 830, a short-term data representation (using, e.g., two-dimensional data, three-dimensional data, or both) may be generated based on the newly captured frame and, optionally, based on one or more previously captured frames. As discussed above, a data representation may be generated by computing spatial characteristics in and around the view in a frame, such as depth, pose, and edges. For example, a short-term data representation may comprise a set of consecutive (or non-consecutive) images and their depth, the pose between each pair of consecutive (or non-consecutive) frames, and a three-dimensional point cloud or surface of the area associated with the short-term data representation. As will be appreciated, additional, less, or different data may be part of the short-term data representation, depending on the specific application and context.

At step 840, the at least one processor may optionally retrieve data associated with a long-term data representation. The data associated with the long-term data representation may be retrieved from a memory, database, or any other source of information. In some embodiments, however, such as when the captured frame is the first frame from which a data representation is generated, no data belonging to a previously stored long-term data representation may be retrieved. Further, in some embodiments, multiple data representations need not be aggregated into a long-term data representation but may rather be generated and stored as singular data representations. At step 850, the generated short-term data representation and the retrieved long-term data representation may be aggregated to form a new, continuous long-term data representation. As discussed above, this may involve detecting overlapping regions in the two data representations, and/or applying a distance threshold or other criteria to determine whether aggregation is warranted. Further, as indicated by the double-arrow between steps 840 and 850, the newly generated long-term data representation may be saved (e.g., in a memory or database) to replace the old, retrieved long-term data representation to be used in a subsequent iteration of method 800. For example, consistent with the description above, a long-term data representation may comprise a sparse set of images and their depth, the pose between pairs of frames, and a three-dimensional point cloud or surface of the area associated with the long-term data representation. As will be appreciated, additional, less, or different data may be part of the long-term data representation, depending on the specific application and context.

At step 860, optional post-processing steps may be performed to the aggregated data representation. For example, an interpolation or a filling algorithm may be applied to address any missing or corrupted information in the aggregated data representation. Other suitable post-processing steps may be applied alone or in combination, such as distortion reduction, noise reduction, shape refinement, and/or other refinement steps. Further, although such steps are shown in FIG. 8 as occurring after aggregation, refinement steps may also be performed both before and after aggregation, only before aggregation, or no refinement steps may be performed altogether. Additionally, the post-processing steps may be performed before saving the newly generated long-term data representation. At step 870, the at least one processor may output information, such as the aggregated data representation (or the singular data representation with no aggregation). As disclosed herein, the aggregated data representation may be used by other processes for determining an examination quality level or value.

Figure 9:
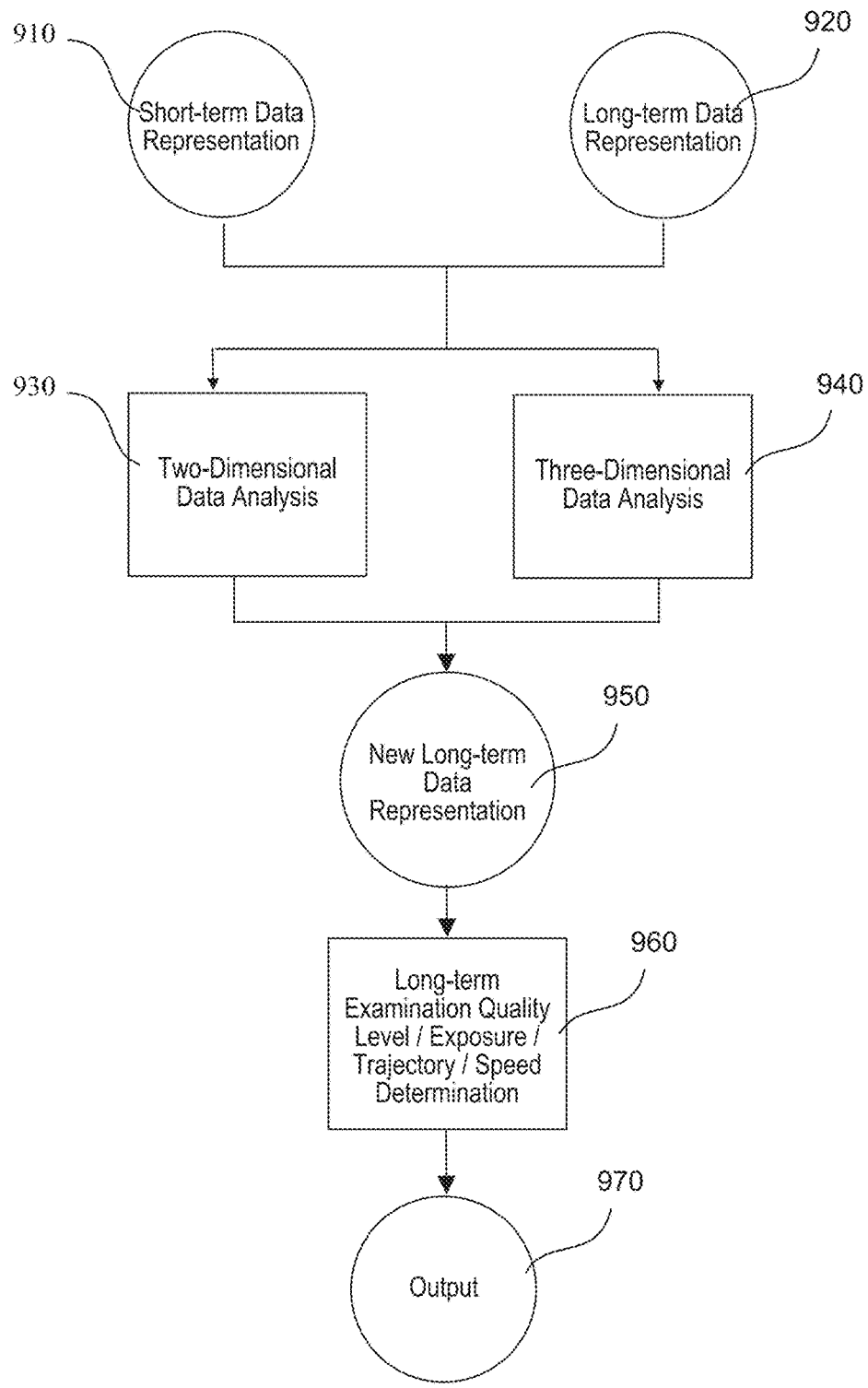
FIG. 9 illustrates an example method for determining a long-term examination quality level and/or other information from short-term and long-term data representations, consistent with embodiments of the present disclosure.

FIG. 9 illustrates an example method 900 for determining a long-term examination quality level and/or other information from short-term and long-term data representations, consistent with embodiments of the present disclosure. Method 900 may be performed concurrently with or following generation of short-term and long-term data representations (e.g., as described above in connection with method 800 of FIG. 8). The example method 900 may be implemented with one or more processors (e.g., the at least one processor of computing device 160 in FIG. 1 or processor(s) 230 in FIG. 2). It will be appreciated that FIG. 9 is a non-limiting example and that modifications may be made to method 900, including by adding, removing, modifying and/or reordering the steps illustrated and described herein.

As shown in FIG. 9, at step 910 a short-term data representation may be generated (e.g., by computing spatial characteristics in and around the view in a frame, such as depth, pose, and edges) and/or retrieved (e.g., from a memory, database, or other source of information). At step 920, a long-term data representation may be generated (e.g., by computing spatial characteristics in and around the view in a frame, such as depth, pose, and edges) and/or retrieved (e.g., from a memory, database, or other source of information). In the example embodiment of method 900, short-term data representation 910 and long-term data representation 920 may include both two-dimensional and three-dimensional information of areas examined by an operator. However, as disclosed herein, the data representations may contain only two-dimensional information, only three-dimensional information, or any combination or type of spatial and/or visual information.

At step 930, two-dimensional information belonging to short-term data representation 910 and long-term data representation 920 may be analyzed to generate a new continuous long-term data representation. Two-dimensional data analysis may be performed using any suitable algorithm, such as by retrieving previously captured frames associated with short-term data representation 910 and long-term data representation 920. Corresponding points and/or features in the previously captured frames may be matched to identify an overlap. The retrieved frames may be transformed or otherwise modified to facilitate analysis, and a correlation or other metric may be computed to determine a best match, including with respect to distinguishable feature points in the short-term and long-term data representations.

At step 940, three-dimensional information belonging to short-term data representation 910 and long-term data representation 920 may also be analyzed to generate a new continuous long-term data representation. Three-dimensional data analysis may be performed using any suitable algorithm to align the short-term and long-term data representations. For example, the three-dimensional analysis may be performed by utilizing a point cloud registration algorithm to identify a spatial transformation that align two or more cloud points, including but not limited to the Iterative Closest Point (ICP) algorithm, the Robust Point Matching (RMP) algorithm, the Kernel Correlation (KC) algorithm, the Coherent Point Drift (CPD) algorithm, the Sorting the Correspondence Space (SCS) algorithm, the Bayesian Coherent Point Drift (BCPD) algorithm, and/or a combination thereof. As another example, the three-dimensional analysis may be performed by utilizing a range imaging algorithm to estimate three-dimensional structures from two-dimensional image frames, including but not limited to the Structure from Motion (SfM) algorithm, the Time-of-Flight (ToF) algorithm, stereo triangulation, sheet of light triangulation, structured light, interferometry, coded aperture, and/or a combination thereof. Corresponding points and/or features in the estimated three-dimensional structures may be matched to identify an overlap. The estimated three-dimensional structures may be transformed or otherwise modified to facilitate analysis, and a correlation or other metric may be computed to determine a best match.

At step 950, a new long-term data representation may result from the analysis of two-dimensional data at block 930 and the analysis of three-dimensional data at block 940. For example, one or more three-dimensional alignment algorithms (e.g., ICP, RMP, KC, CPD, SCS, and/or BCPD algorithms) may be utilized to first obtain a rough alignment between the short-term and the long-term data representations using their respective three-dimensional data (e.g., three-dimensional point clouds). Next, one or more two-dimensional alignment algorithms (e.g., keypoint matching and/or image registration algorithms) may be utilized to perform a fine alignment between the short-term and the long-term data representations using their respective two-dimensional data (e.g., image frames). Other approaches that utilize three-dimensional and/or two-dimensional information may also be used, as would be appreciated by those skilled in the art upon reading this disclosure. For example, an alternative approach may include iteratively minimizing the alignment error based on the three-dimensional and/or two-dimensional data. Accordingly, in some embodiments, by combining the two-dimensional information (e.g., through image retrieval) and three-dimensional information (e.g., through point cloud registration), the accuracy of the new long-term data representation may be maximized through merging the short-term data to the long-term data. Further, at step 960, information associated with the quality of the operator's examination in view of new long-term data representation 950 may be computed. As shown in FIG. 9, for example, a long-term examination quality level, a long-term trajectory, and/or a long-term speed determination may be calculated. For example, the total area of new long-term data representation 950 may be compared to a model surface to determine a long-term examination quality level. Moreover, a camera trajectory during capture of short-term data representation 910 and long-term data representation 920 may be calculated (if not previously calculated) and combined to arrive at a long-term trajectory for new long-term data representation 950. Similarly, a camera speed during capture of short-term data representation 910 and long-term data representation 920 may be calculated (if not previously calculated) and combined to arrive at a long-term speed for new long-term data representation 950. At step 970, information may be outputted, such as the long-term examination quality level, trajectory, speed, and/or any other information associated with estimating the quality of the operator's examination of the new long-term data representation calculated at step 960.

When building a three-dimensional representation for the colon surface, each three-dimensional point may be recorded with one or more of the following information: best and average direction of observation; closest and average distance from camera; time of exposure; and speed of exposure. For example, it could happen that some areas of the mucosa surface are observed only from far away. As such, in some embodiments, a binary mask is not only produced for exposure observation (like FIG. 10, described below) but also a heatmap is generated where for each pixel or area the color is associated with the quality of observation, from very high quality (e.g., nearby, normal to surface, slow speed) to zero quality (e.g., never in endoscope field of view). In some embodiments, a heat map could be computed or visualized on a three-dimensional model or on a flat, two-dimensional projection (like FIG. 10, described below).

Figure 10:
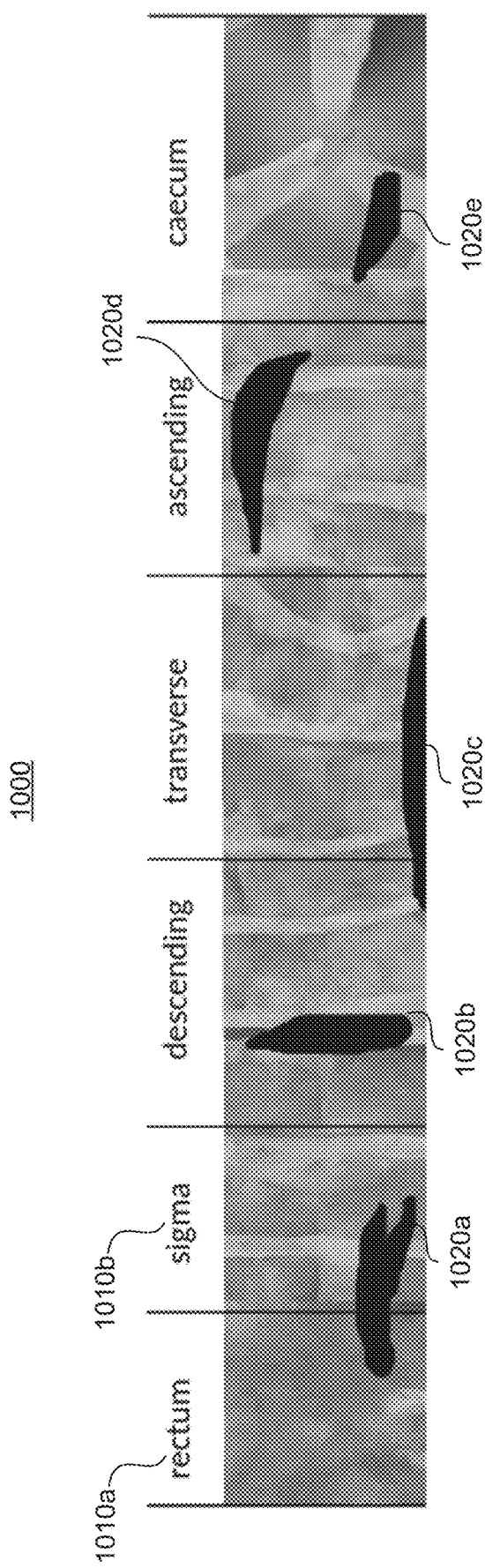
FIG. 10 illustrates an example long-term data representation, consistent with embodiments of the present disclosure.

FIG. 10 illustrates an example long-term data representation 1000, consistent with disclosed embodiments. As shown in FIG. 10, example long-term data representation 1000 may be represented as a cylindrical projection of a patient's organ, in this case a colon, examined during a procedure. A long-term data representation may be represented as other shapes, however, depending on the specific organ or area examined. Moreover, although depicted as an image for purposes of this illustration, it is to be understood that a long-term data representation may comprise a variety of information, whether two-dimensional and/or three-dimensional, such as one or more images, depth data, pose data, and/or a three-dimensional point cloud or surface data. As further shown in FIG. 10, long-term data representation 1000 may be separated into multiple anatomical segments, such different parts of the colon including the rectum, the sigma, the descending colon, the transverse colon, the ascending colon, or the caecum. Long-term data representation 1000 may indicate areas examined by an operator during the examination, shown in FIG. 10 as grayscale areas that resemble an anatomical structure or implemented as colored areas on a display device for an operator (not shown). Conversely, dark areas, such as areas 1020a, 1020b, 1020c, 1020d, and 1020e may indicate areas that the operator examined poorly or did not examine at all. As further shown, a dark area may span across multiple anatomical segments, as illustrated by area 1020a spanning across rectum segment 1010a and sigma segment 1010b. Accordingly, long-term data representation 1000 may be used to track the examination quality level (or any other attribute, such as speed, trajectory, or exposure) of the operator during the entire medical procedure or a portion thereof.

Figure 11:
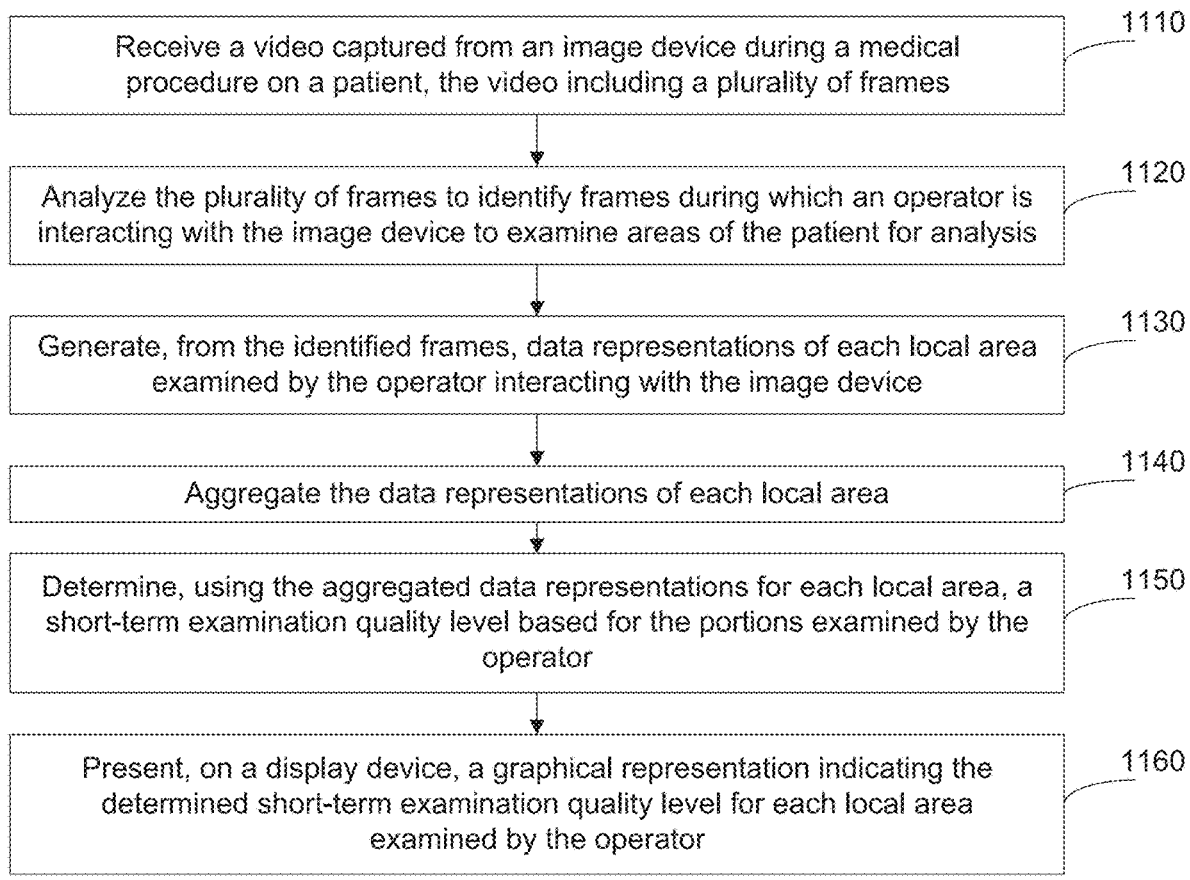
FIG. 11 illustrates an example method for processing video captured during a medical procedure, consistent with embodiments of the present disclosure.

FIG. 11 illustrates an example method 1100 for processing video captured during a medical procedure, consistent with embodiments of the present disclosure. The example method 1100 may be implemented with the aid of at least one processor (e.g., the at least one processor of computing device 160 in FIG. 1 or processor(s) 230 in FIG. 2). It will be appreciated that FIG. 11 is a non-limiting example and that modifications may be made to method 1100, including by adding, removing, modifying and/or reordering the steps illustrated and described herein.

As shown in FIG. 11, at step 1110 the at least one processor may receive real-time video captured from an image device during a medical procedure on a patient, the real-time video including a plurality of frames. At step 1120, the at least one processor may analyze the plurality of frames to identify frames during which an operator is interacting with the image device to examine areas of the patient for analysis. As disclosed herein, an operator's type of interaction with the image device may be determined by analyzing and classifying frames into one or more of a plurality of actions using any suitable image classification algorithm, trained neural network, or a combination of both. At step 1130, the at least one processor may generate, from the identified frames, data representations of each local area examined by the operator interacting with the image device. As used herein, a "local area" may correspond to an area currently being analyzed by the operator. Data representations may be generated by computing spatial characteristics in and around the view in a frame, such as depth, pose, and edges. As will be appreciated from this disclosure, other visual attributes may be used to generate the data representations. At step 1140, the at least one processor may aggregate the data representations of each local area. The data representations of each local area may be aggregated by joining representations that are adjacent to one another in the areas examined by the operator, as described herein. In some embodiments, data representations of two or more local areas may be aggregated to create a data representation of areas analyzed by the operator during an entire medical procedure or a portion thereof to create a long-term data representation. At step 1150, the at least one processor may determine, using the aggregated data representations for each local area, a short-term examination quality level for the portions examined by the operator. The short-term examination quality level may be determined, for example, by calculating a ratio between a local area examined by the operator and an area of a model surface, the trajectory of the image device, the speed of the image device, and/or any other information available to or generated by the computing device. At step 1160, the at least one processor may present, on a display device during the medical procedure, a graphical representation indicating the short-term examination quality level for each local area examined by the operator. The determined examination quality level may be presented in any desired format, such as percentage values, classification labels, alphanumeric characters, colors, images, videos, graphs, or any other format. In addition, as disclosed herein, other information or statistics may be displayed along with the determined examination quality level.

FIGS. 12A and 12B illustrate exemplary graphical representations for indicating examination quality levels and/or other attributes of the operator's navigation (e.g., speed, trajectory, and/or exposure), consistent with disclosed embodiments. The graphical representations of FIGS. 12A and 12B or similar representations may be updated and presented for display following each examination quality level determination or determination of any other attribute of the operator's navigation, as described herein. Such graphical representations may be displayed separately (e.g., on a separate display or output) or as augmenting information that is overlaid with the real-time video from the image device (e.g., on display 180). In some embodiments, the information associated with the examination quality level, trajectory, speed, exposure, and/or other attributes of the examination may be displayed as part of one or more graphical representations. For example, a graphical representation of an examination quality level may be combined and/or include a graphical representation of other determined information (e.g., speed and/or trajectory information). The exemplary information of FIGS. 12A and 12B may be determined and presented during a medical procedure to provide feedback on the examination quality level, trajectory, speed, exposure, and/or other attributes of the examination during the medical procedure. Further, the information associated with the examination quality level or any other attribute may be updated and displayed in real-time during a medical procedure (e.g., at predetermined time intervals) as a result of an operator's actions.

In FIG. 12A, for example, an example graphical representation 1200A for examination quality level and/or other attributes of the operator's navigation is shown that includes a series of sections arranged as rings. A ring, such as ring 1210, may comprise one or more sections 1212, 1214, 1216, and 1218. Each ring may represent a different depth along a view in one or more frames. For example, the innermost ring 1210 may represent areas in the frame farthest away from the image device, while the outermost ring 1230 may represent areas in the frame closest to the image device. Although rings 1210, 1220, and 1230 are illustrated as concentric rings, other arrangements such as non-concentric rings may be used, as appropriate. Further, each section of the rings may have different colors, indicating the examination quality level, trajectory, speed, exposure, and/or other attributes of the examination in each section. For example, a color of green may indicate that the examination quality level (or any other attribute) of the surface corresponding to that section is high, while a color of red may indicate that the examination quality level (or any other attribute) of the surface corresponding to that section is low. As the examination quality level is determined iteratively during a medical procedure, the displayed colors may be updated and change to reflect the operator's examination of an organ of a patient, as mentioned above. In some embodiments, each section of a ring may be represented by a different visual characteristic including, but not limited to, a color, a pattern, a shape, or other characteristics.

In FIG. 12B, another example is provided of a graphical representation reflecting an examination quality level and/or other attributes of the operator's navigation. In this example, graphical representation is based on a model 1200B of the examined area, such as a patient's colon, as shown in FIG. 12B. The model 1200B may be two-dimensional, three-dimensional, or a combination of both. As illustrated, model 1200B may be represented as comprising one or more sections. Each section, such as sections 1240, 1242, or 1244, in the colon may represent one or more surfaces examined by the operator during a medical procedure. Each section may have different colors, indicating the examination quality level, trajectory, speed, exposure, and/or other attributes of the examination in each section. As with FIG. 12A, for example, a color of green may indicate that the examination quality level (or any other attribute) of the surface corresponding to that section is high, while a color of red may indicate that the examination quality level (or any other attribute) of the surface corresponding to that section is low. The colors may update and/or change during the medical procedure, as mentioned above. It is to be understood that other graphical representations may be used to indicate examination quality levels and the examples of FIGS. 12A and 12B are not limiting to the scope of the present disclosure.

Figure 13A:
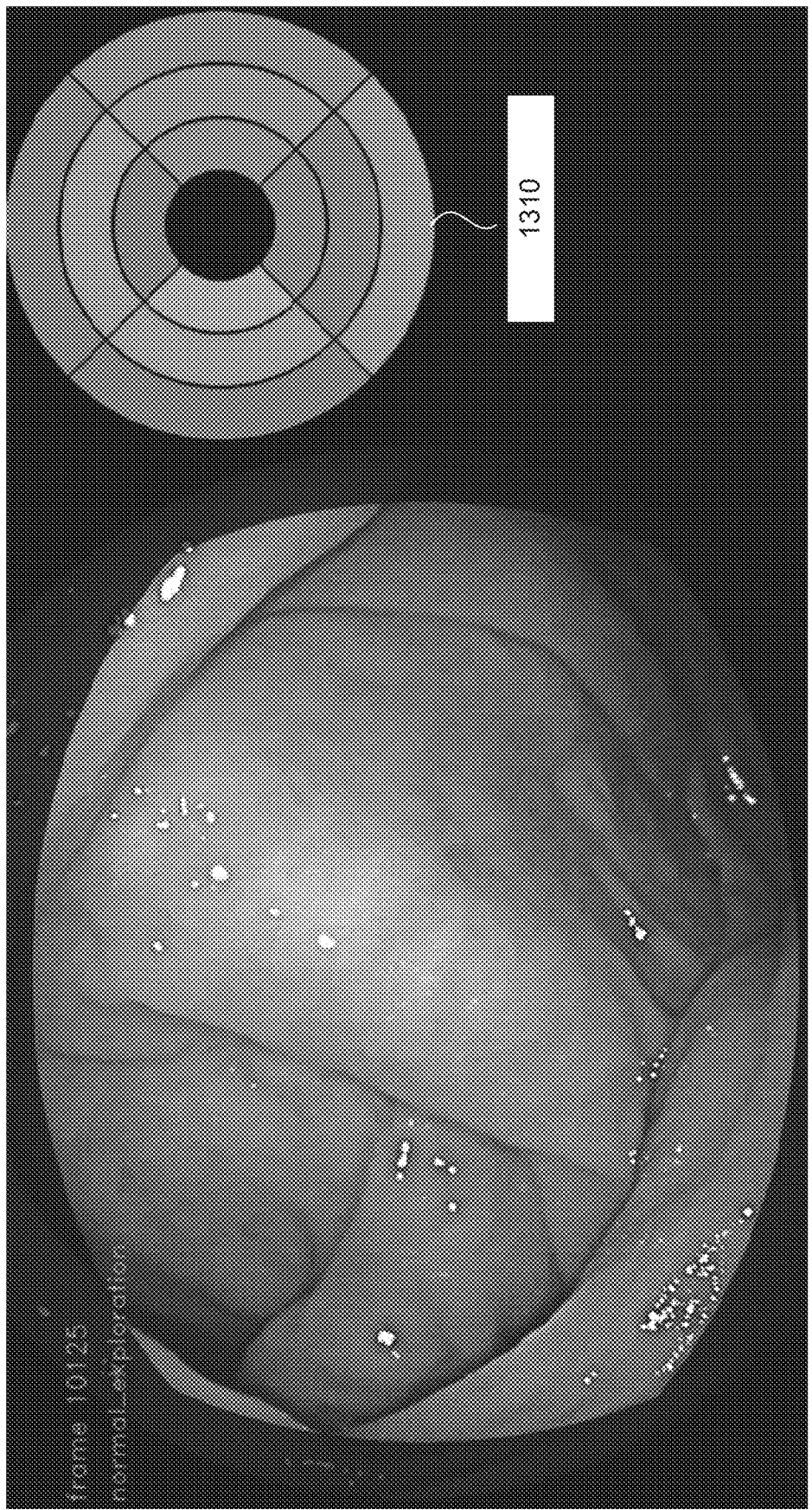
FIGS. 13A-13C illustrate further examples of graphical representations for indicating examination quality levels and/or other attributes of the operator's navigation, consistent with embodiments of the present disclosure.
Figure 13B:
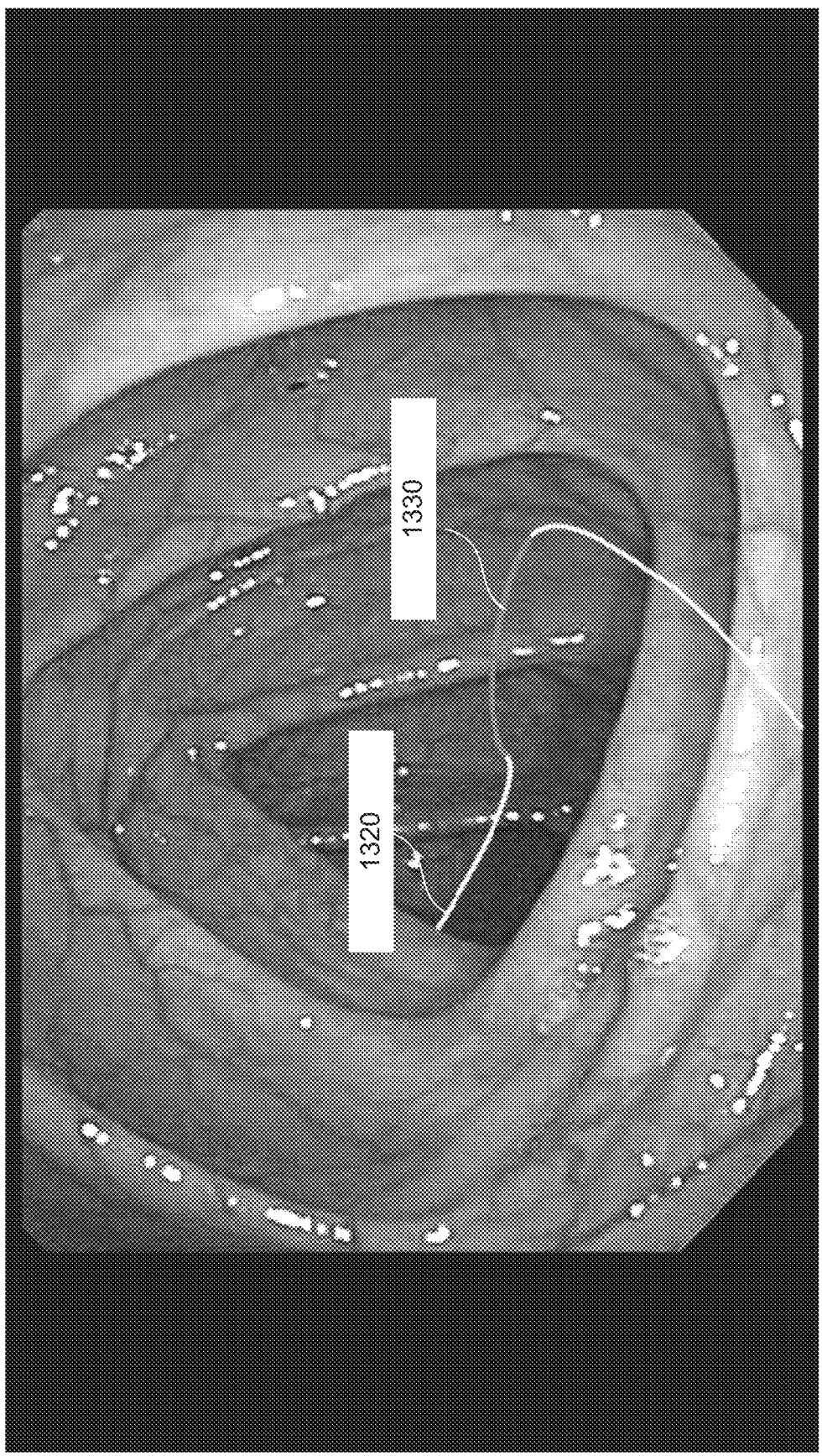
Figure 13C:
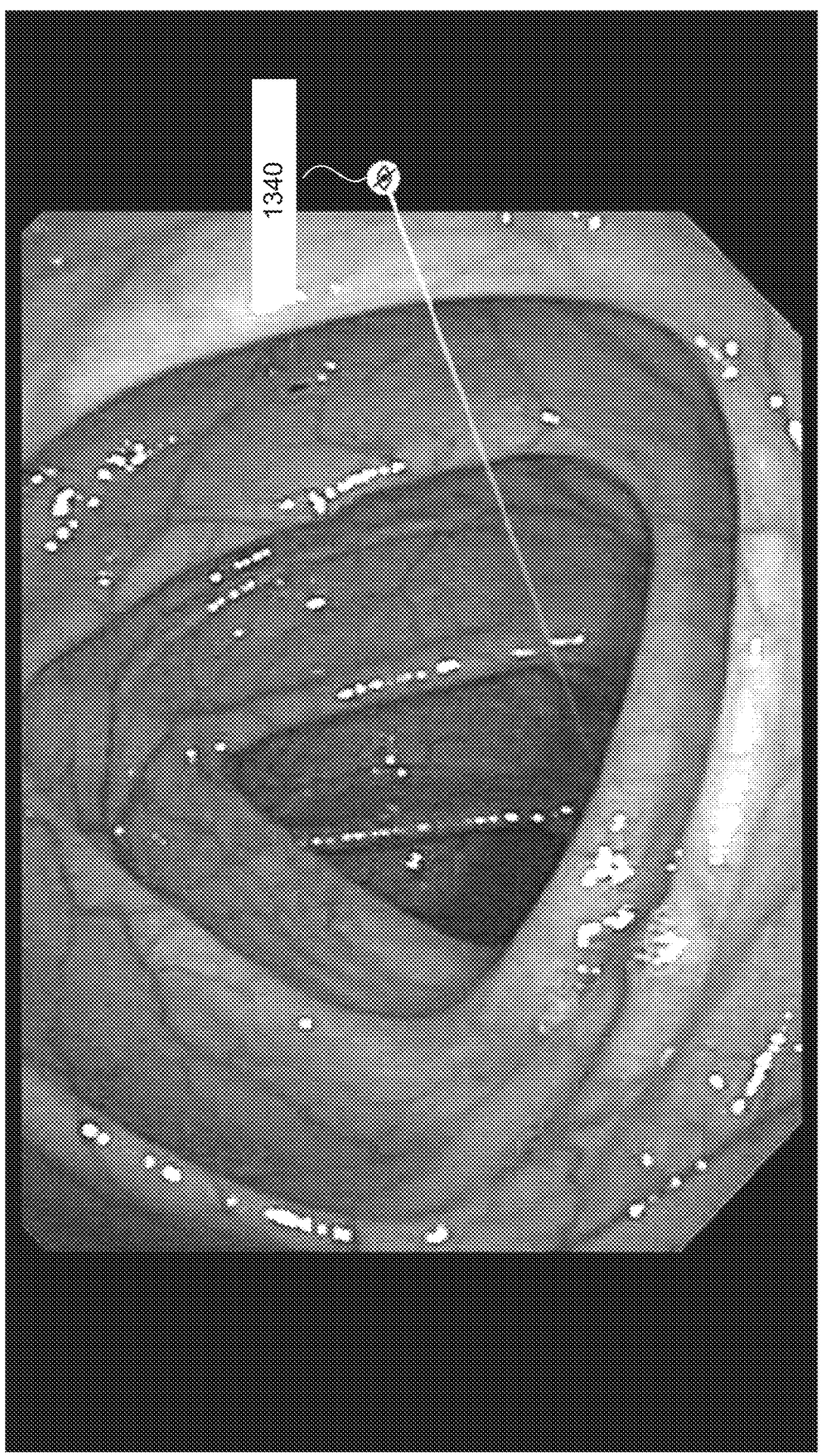

FIGS. 13A, 13B, and 13C illustrate exemplary graphical representation for indicating examination quality levels and/or other attributes of the operator's navigation (e.g., speed, trajectory, or exposure), consistent with disclosed embodiments. As shown, the exemplary graphical representations of FIGS. 13A-13C are provided as overlays or modifying information to a video frame. These graphical representations may be updated and presented for display (e.g., on display 180) during a medical procedure to provide feedback to an operator on the examination quality level trajectory, speed, exposure, and/or other attributes of the examination during the medical procedure. Further, the exemplary information of FIGS. 13A-13C may be updated in real-time during the medical procedure as a result of an operator's actions.

FIG. 13A, for example, depicts an example graphical representation 1310 for indicating an examination quality level and/or other attributes of the operator's navigation that includes a series of sections arranged as three rings, similar to the graphical representation of FIG. 12A. As with FIG. 12A, each ring may represent a different depth along the view of the image frame shown in FIG. 13A. For example, the innermost ring may represent areas in the frame farthest away from the image device within the image frame, while the outermost ring may represent areas in the frame closest to the image device. Further, consistent with the description above, each section of the rings may have different colors, indicating the examination quality level, trajectory, speed, exposure, and/or other attributes of the examination in each section. For example, a color of green may indicate that the examination quality level (or any other attribute) of the surface corresponding to that section is high, while a color of red may indicate that the examination quality level (or any other attribute) of the surface corresponding to that section is low. As the examination quality level is determined iteratively during a medical procedure, the displayed colors may be updated and change to reflect the operator's examination of an organ of a patient, as discussed above.

In FIG. 13B, another example is provided of a graphical representation reflecting an examination quality level and/or other attributes of the operator's navigation that is overlaid over an image frame. In this example, the graphical representation may be based on the trajectory taken by the operator during the medical procedure, although a graphical representation may be based on other factors or attributes of the operator's navigation. As shown in FIG. 13B, the graphical representation may be a line of varying colors that may indicate the examination quality level, trajectory, speed, exposure, and/or other attributes at that location. For example, line segment 1320 may be green to indicate a high examination quality level (or any other attribute) of the examination. Similarly, line segment 1330 may be red to indicate a low examination quality level (or any other attribute) of the navigation. Further, although shown as a continuous line, any other graphical representation may be used, such as dots, arrows, intermittent lines, icons, letters (e.g., "GOOD" or "BAD"), or any other visual representations. The colors may update and/or change during the medical procedure, as mentioned above.

FIG. 13C illustrates another exemplary graphical representation reflecting an examination quality level and/or other attributes of the operator's navigation that is overlaid over an image frame. In this example, the graphical representation may be used to bring attention to a certain area in the patient's organ that the operator may have examined poorly or may have missed entirely. As shown in FIG. 13C, an image such as icon 1340 may be used to point to the area of attention. In some embodiments, icon 1340 may be displayed concurrently with another graphical representation (e.g., graphical representations 1310 of FIG. 13A or 1320/1330 of FIG. 13B), or the graphical representations may alternate between one another (e.g., based on time, distance from the area of attention, or as a result of an operator action such as a button press or through a change in setting). Although icon 1340 of FIG. 13C is shown as an eye with a slash through it, it is to be understood that any other visual representation may be used to bring attention to the area, such as words (e.g., "MISSED AREA"), shapes (e.g., an arrow), other icons, or other graphical representation or icon. The icon and/or any of its visual attributes (e.g., color or size) may be updated and change during the medical procedure, as mentioned above. It is to be understood that other graphical representations may be used to indicate examination quality levels and/or any other attribute and the examples of FIGS. 13A-13C are not limiting to the scope of the present disclosure.

The diagrams and components in the figures described above illustrate the architecture, functionality, and operation of possible implementations of systems, methods, and computer hardware or software products according to various example embodiments of the present disclosure. For example, each block in a flowchart or diagram may represent a module, segment, or portion of code, which includes one or more executable instructions for implementing the specified logical functions. It should also be understood that in some alternative implementations, functions indicated in a block may occur out of order noted in the figures. By way of example, two blocks or steps shown in succession may be executed or implemented substantially concurrently, or two blocks or steps may sometimes be executed in reverse order, depending upon the functionality involved. Furthermore, some blocks or steps may be omitted. It should also be understood that each block or step of the diagrams, and combination of the blocks or steps, may be implemented by special purpose hardware-based systems that perform the specified functions or acts, or by combinations of special purpose hardware and computer instructions. Computer program products (e.g., software or program instructions) may also be implemented based on the described embodiments and illustrated examples.

It should be appreciated that the above-described systems and methods may be varied in many ways and that different features may be combined in different ways. In particular, not all the features shown above in a particular embodiment or implementation are necessary in every embodiment or implementation. Further combinations of the above features and implementations are also considered to be within the scope of the herein disclosed embodiments or implementations.

While certain embodiments and features of implementations have been described and illustrated herein, modifications, substitutions, changes and equivalents will be apparent to those skilled in the art. It is, therefore, to be understood that the appended claims are intended to cover all such modifications and changes that fall within the scope of the disclosed embodiments and features of the illustrated implementations. It should also be understood that the herein described embodiments have been presented by way of example only, not limitation, and various changes in form and details may be made. Any portion of the systems and/or methods described herein may be implemented in any combination, except mutually exclusive combinations. By way of example, the implementations described herein can include various combinations and/or sub-combinations of the functions, components and/or features of the different embodiments described.

Moreover, while illustrative embodiments have been described herein, the scope of the present disclosure includes any and all embodiments having equivalent elements, modifications, omissions, combinations (e.g., of aspects across various embodiments), adaptations or alterations based on the embodiments disclosed herein. Further, elements in the claims are to be interpreted broadly based on the language employed in the claims and not limited to examples described herein or during the prosecution of the present application. Instead, these examples are to be construed as non-exclusive. It is intended, therefore, that the specification and examples herein be considered as exemplary only, with a true scope and spirit being indicated by the following claims and their full scope of equivalents.

What is claimed is:

1. A computer-implemented system for processing a video captured during a medical procedure, the system comprising:

at least one processor configured to, during a medical procedure performed on a patient:
receive a video captured from an image device during a medical procedure on a patient, the video including a plurality of frames;
identify frames from the video during which an operator is interacting with the image device to examine areas of an organ of the patient for analysis;
generate, from the identified frames, data representations of a first area examined by the operator interacting with the image device;
further generate, from the identified frames, data representations of one or more further areas examined by the operator interacting with the image device;
aggregate the data representations of the first area with the data representations of the one or more further areas;
determine, using the aggregated data representations, an examination quality level of the areas examined by the operator based on at least a ratio between the areas examined by the operator and an area of a model surface; and
present, on a display device, a graphical representation indicating the determined examination quality level of the areas examined by the operator.

2. The system of claim 1, wherein the at least one processor is further configured to determine the examination quality level based on at least a trajectory of the image device, a speed of the image device, and the ratio between the areas examined by the operator and the area of the model surface.

3. The system of claim 1, wherein the data representations for the first area and the one or more further areas include at least one of two-dimensional data and three-dimensional data.

4. The system of claim 1, further comprising a neural network adapted to perform a contextual evaluation to identify frames among the plurality of frames of a real-time video during which the operator is interacting with the image device to examine areas of the patient for analysis.

5. The system of claim 1, wherein the at least one processor is further configured to determine the examination quality level on a real-time basis during the medical procedure; update the determined examination quality level as the medical procedure is performed on the patient; and modify the graphical representation as the determined examination quality level is updated during the medical procedure.

6. The system of claim 5, wherein the modification to the graphical representation includes modification to at least one of a color and an alphanumeric character indicating the examination quality level.

7. The system of claim 5, wherein modifying the graphical representation includes a modification that visually indicates a low examination quality level based on a threshold of the ratio between the areas examined by the operator and the area of the model surface.

8. The system of claim 1, wherein the at least one processor is further configured to generate a short-term data representation for an area examined by the operator, and a long-term data representation for a plurality of areas examined by the operator during the medical procedure performed on the patient.

9. The system of claim 8, wherein the at least one processor is further configured to: determine a short-term examination quality level using the short-term data representation; and determine a long-term examination quality level using the long-term data representation.

10. The system of claim 1, wherein the medical procedure comprises an endoscopy, an esophagogastroduodenoscopy, a colonoscopy, a sigmoidoscopy, an endoscopic cholangiopancreatography, or an enteroscopy.

11. The system of claim 1, wherein the at least one processor is further configured to:
generate, from the identified frames, a first three-dimensional representation of the examined first area of the patient;
further generate, from the identified frames, a second three-dimensional representation of an examined second area of the patient;
determine a proximity of the first three-dimensional representation to the second three-dimensional representation in three-dimensional space;
merge at least a portion of the first three-dimensional representation with at least a portion of the second three-dimensional representation when the determined proximity is within a threshold; and
identify, using the merged portions of the first and second three-dimensional representations, areas not examined by the operator during the medical procedure.

12. The system of claim 11, wherein the at least one processor is further configured to generate a graphical representation indicating a ratio between the areas examined by the operator and the areas not examined by the operator.

13. The system of claim 1, wherein the examination quality is further based on a trajectory of the image device.

14. A method for processing a video, the method comprising the following operations performed by at least one processor:
during a medical procedure performed on a patient:
receiving a video captured from an image device during a medical procedure on a patient, the video including a plurality of frames;
identifying frames from the video during which an operator is interacting with the image device to examine areas of an organ of the patient for analysis;
generating, from the identified frames, data representations of a first area examined by the operator interacting with the image device;
further generating, from the identified frames, data representations of one or more further areas examined by the operator interacting with the image device;
aggregating the data representations of the first area with the data representations of the one or more further areas;
determining, using the aggregated data representations, an examination quality level of the areas examined by the operator based on at least a ratio between the areas examined by the operator and an area of a model surface; and
presenting, on a display device, a graphical representation indicating the determined examination quality level of the areas examined by the operator.

15. The method of claim 14, further comprising determining the examination quality level based on at least a trajectory of the image device, a speed of the image device, and the ratio between the areas examined by the operator and the area of the model surface.

16. The method of claim 14, wherein the data representations for the first area and the one or more further areas include at least one of two-dimensional data and three-dimensional data.

17. The method of claim 14, further comprising performing, using a neural network, a contextual evaluation to identify frames among the plurality of frames of a real-time video during which the operator is interacting with the image device to examine areas of the patient for analysis.

18. The method of claim 14, further comprising determining the examination quality level on a real-time basis during the medical procedure; update the determined examination quality level as the medical procedure is performed on the patient; and modifying the graphical representation as the determined examination quality level is updated during the medical procedure.

19. The method of claim 18, wherein modifying the graphical representation includes modifying at least one of a color and an alphanumeric character indicating the examination quality level.

20. The method of claim 18, wherein modifying the graphical representation includes a modification that visually indicates a low examination quality level based on a threshold of the ratio between the areas examined by the operator and the area of the model surface.

21. The method of claim 14, further comprising generating a short-term data representation for an area examined by the operator, and a long-term data representation for a plurality of areas examined by the operator during the medical procedure performed on the patient.

22. The method of claim 21, further comprising: determining a short-term examination quality level using the short-term data representation; and determining a long-term examination quality level using the long-term data representation.

23. The method of claim 14, wherein the medical procedure comprises an endoscopy, an esophagogastroduodenoscopy, a colonoscopy, a sigmoidoscopy, an endoscopic cholangiopancreatography, or an enteroscopy.

24. The method of claim 14, further comprising the following operations performed by the at least one processor:
generating, from the identified frames, a first three-dimensional representation of the examined first area of the patient;
further generating, from the identified frames, a second three-dimensional representation of an examined second area of the patient;
determining a proximity of the first three-dimensional representation to the second three-dimensional representation in three-dimensional space;
merging at least a portion of the first three-dimensional representation with at least a portion of the second three-dimensional representation when the determined proximity is within a threshold; and
identifying, using the merged portions of the first and second three-dimensional representations, areas not examined by the operator during the medical procedure.

25. The method of claim 24, further comprising generating a graphical representation indicating a ratio between the areas examined by the operator and the areas not examined by the operator.

26. The method of claim 14, wherein the examination quality is further based on a trajectory of the image device.

* * * * *